United States Patent
Hirai et al.

(10) Patent No.: US 9,833,280 B2
(45) Date of Patent: Dec. 5, 2017

(54) GRASPING TREATMENT DEVICE

(71) Applicant: OLYMPUS CORPORATION, Tokyo (JP)

(72) Inventors: Yuji Hirai, Ebina (JP); Eiji Murakami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 41 days.

(21) Appl. No.: 14/720,073

(22) Filed: May 22, 2015

(65) Prior Publication Data

US 2015/0297289 A1     Oct. 22, 2015

Related U.S. Application Data

(63) Continuation of application No. PCT/JP2014/065133, filed on Jun. 6, 2014.

(30) Foreign Application Priority Data

Jun. 7, 2013   (JP) ................... 2013-121189

(51) Int. Cl.
*A61B 17/32* (2006.01)
*A61B 18/14* (2006.01)
(Continued)

(52) U.S. Cl.
CPC .. *A61B 18/1445* (2013.01); *A61B 17/320092* (2013.01); *A61B 18/1482* (2013.01);
(Continued)

(58) Field of Classification Search
CPC ............ A61B 18/1445; A61B 18/1482; A61B 2018/00077; A61B 2018/00083
See application file for complete search history.

(56) References Cited

U.S. PATENT DOCUMENTS

2009/0088743 A1   4/2009   Masuda
2012/0277778 A1   11/2012  Masuda et al.
2013/0046306 A1   2/2013   Evans et al.

FOREIGN PATENT DOCUMENTS

CN   101427937 A   5/2009
EP   1875875 A1    1/2008
(Continued)

OTHER PUBLICATIONS

Jul. 8, 2014 International Search Report issued in International Application No. PCT/JP2014/065133.
(Continued)

*Primary Examiner* — Michael Peffley
*Assistant Examiner* — Samantha Good
(74) *Attorney, Agent, or Firm* — Oliff PLC

(57) ABSTRACT

A jaw of a grasping treatment device includes a non-contact portion having a space between it and a distal treatment section in a state where an abutment portion abuts on the distal treatment section, and the non-contact portion includes a wall surface portion inclined so that it is extended toward a distal treatment section side as it is extended away from the abutment portion. A movement regulating portion is provided in a region of the non contact portion located closer to the abutment portion than a continuous surface which forms an edge of the non-contact portion. The movement regulating portion located in the first wall surface portion regulates a movement of a grasp object along the jaw axis direction.

6 Claims, 18 Drawing Sheets

(51) Int. Cl.
      *A61B 18/00*        (2006.01)
      *A61B 17/28*        (2006.01)
      *A61B 90/00*        (2016.01)
(52) U.S. Cl.
      CPC ............... *A61B 2017/2825* (2013.01); *A61B 2018/00077* (2013.01); *A61B 2018/00083* (2013.01); *A61B 2018/00273* (2013.01); *A61B 2018/00994* (2013.01); *A61B 2018/1457* (2013.01); *A61B 2090/036* (2016.02)

(56) References Cited

FOREIGN PATENT DOCUMENTS

| | | |
|---|---|---|
| JP | 2009-160404 A | 7/2009 |
| WO | 2011/099571 A1 | 8/2011 |

OTHER PUBLICATIONS

Dec. 8, 2015 International Preliminary Report on Patentability issued in International Patent Application No. PCT/JP2014/065133.
Apr. 6, 2017 Office Action issued in Chinese Patent Application No. 201480032567.5.
Jan. 12, 2017 Extended European Search Report issued in European Application No. 14807774.6.

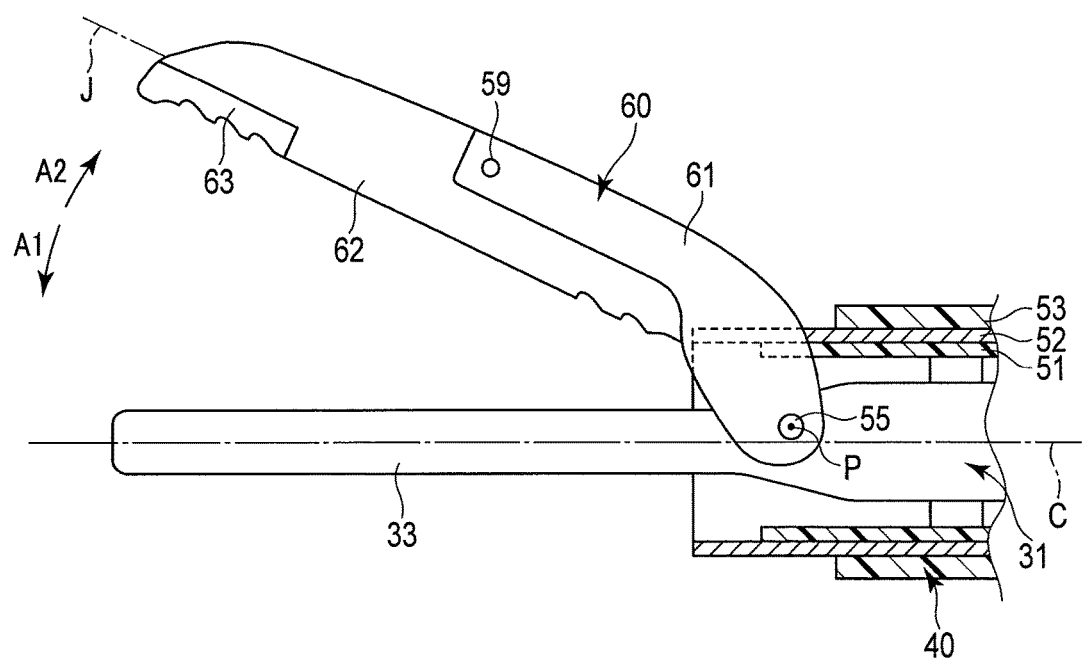
F I G. 4

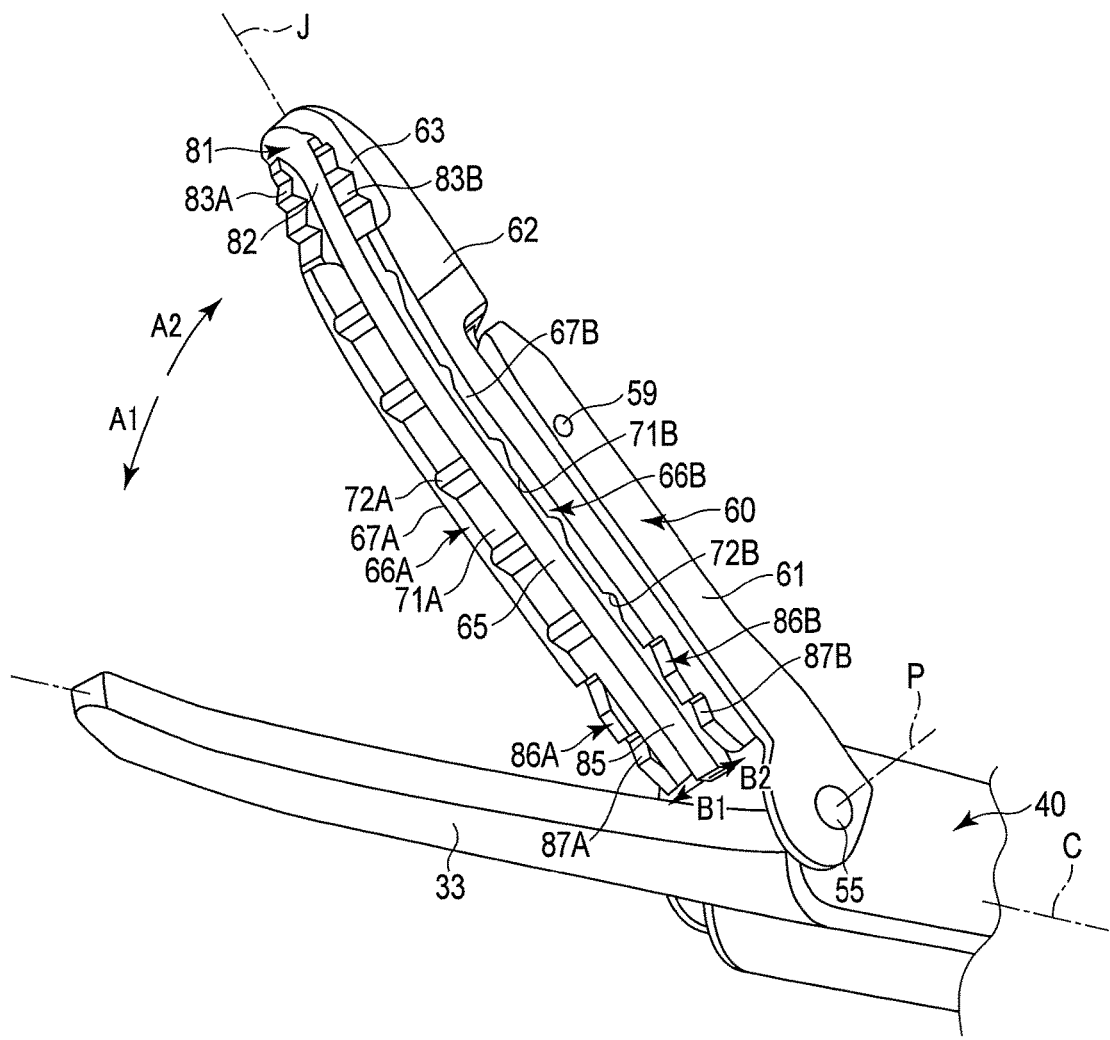
F I G. 5

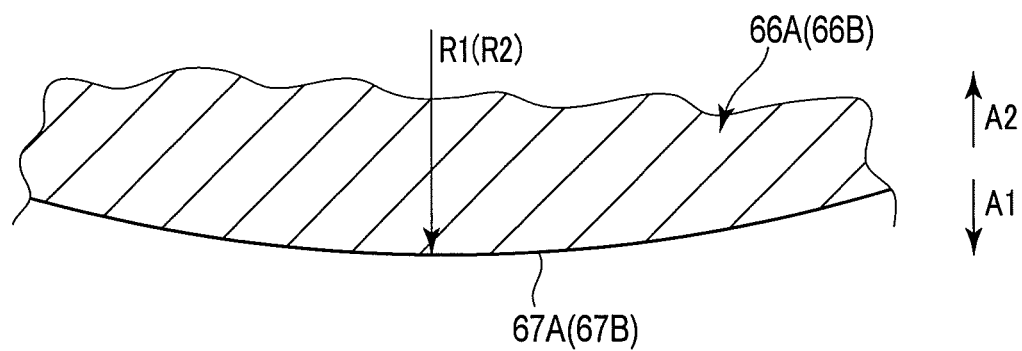
F I G. 12
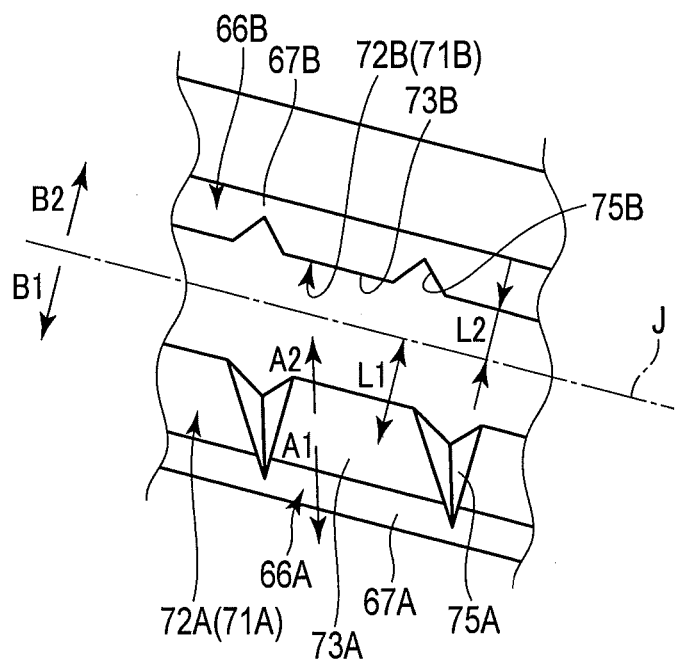
F I G. 13

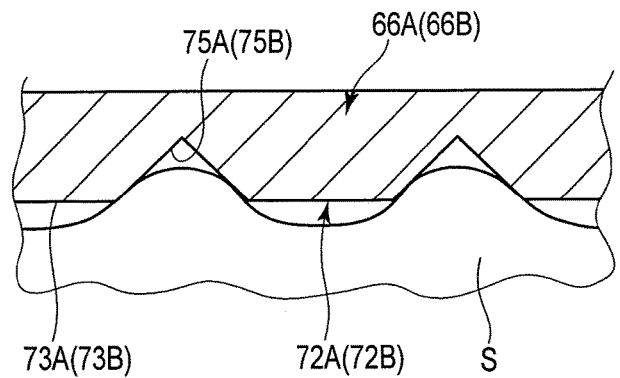
F I G. 14
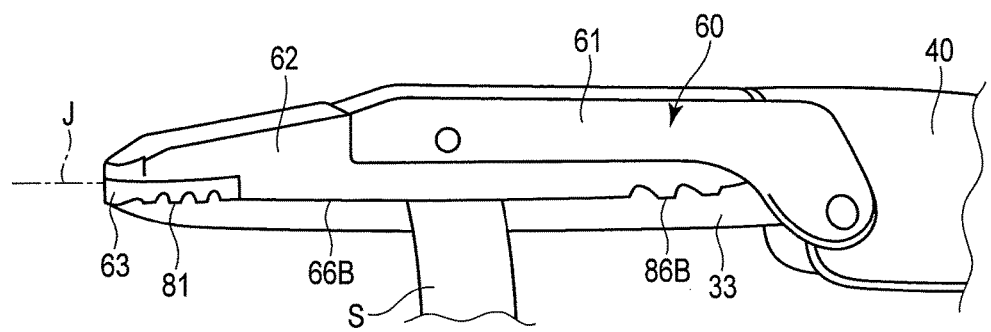
F I G. 15
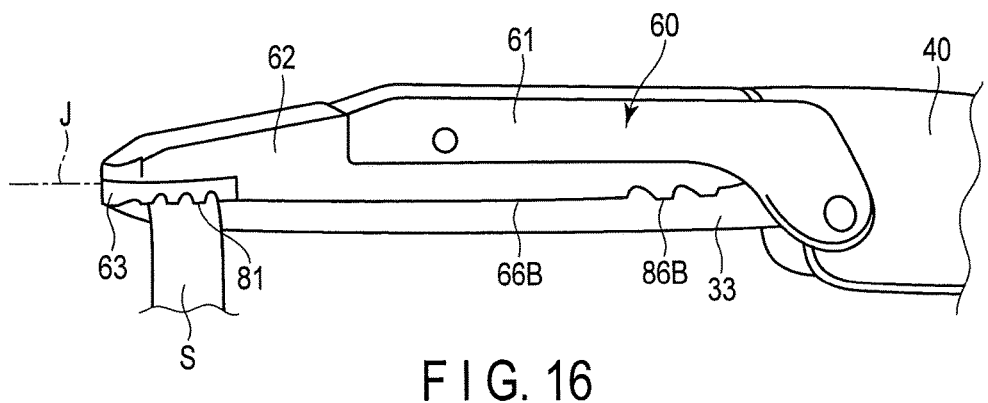
F I G. 16

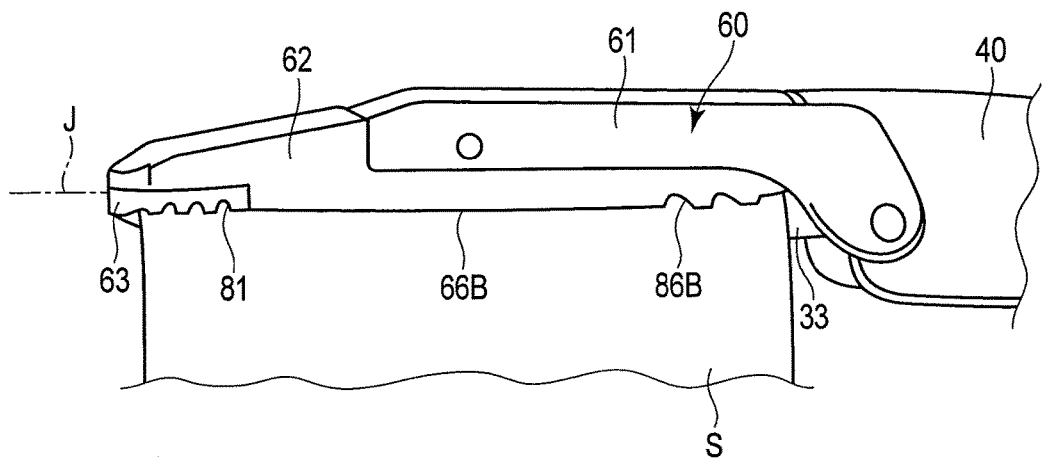
F I G. 17
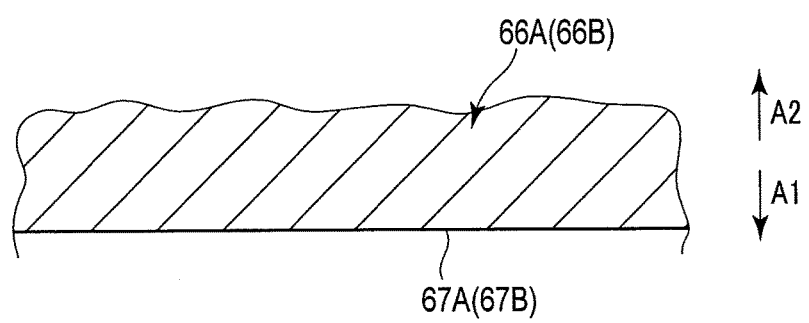
F I G. 18

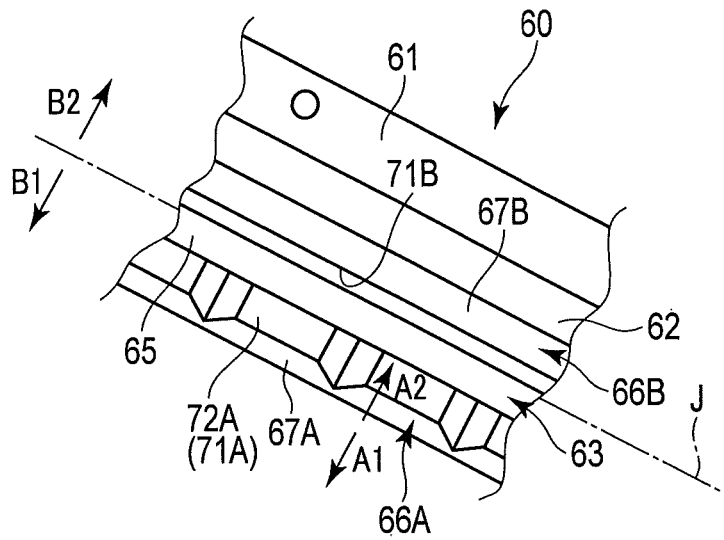
F I G. 19
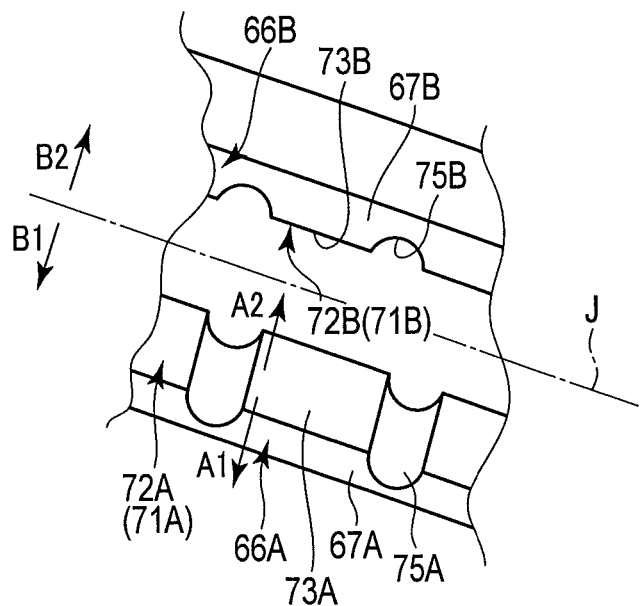
F I G. 20

GRASPING TREATMENT DEVICE

CROSS-REFERENCE TO RELATED APPLICATIONS

This is a Continuation Application of PCT Application No. PCT/JP2014/065133, filed Jun. 6, 2014 and based upon and claiming the benefit of priority from prior Japanese Patent Application No. 2013-121189, filed Jun. 7, 2013, the entire contents of which are incorporated herein by reference.

BACKGROUND OF THE INVENTION

1. Field of the Invention

The present invention relates to a grasping treatment device which includes a probe having a distal treatment section disposed in a distal portion thereof, and a jaw that is a grasping unit openable and closable relative to the distal treatment section, and which is capable of grasping a grasp object between the distal treatment section and the jaw.

2. Description of the Related Art

In Jpn. Pat. Appln. KOKAI Publication No. 2009-160404, there is disclosed a grasping treatment device including a probe which is extended along a longitudinal axis and in a distal end of which a distal treatment section is disposed, and a jaw which is a grasping unit openable and closable relative to the distal treatment section. In the grasping treatment device, it is possible to grasp a grasp object such as a biological tissue between the distal treatment section and the jaw, and in a state where the grasp target is grasped between the distal treatment section and the jaw, a treatment of the grasp object is performed. The jaw is extended along a jaw axis, and includes an abutment portion that can abut on the distal treatment section in a state where the jaw is closed relative to the distal treatment section. Here, directions that are perpendicular to the jaw axis and perpendicular to a jaw opening-or-closing direction are defined as a first jaw width direction and a second jaw width direction. The jaw includes a first non-contact portion which is provided to face the distal treatment section on a first jaw width direction side with respect to the abutment portion, and which has a space between it and the distal treatment section in a state where the abutment portion abuts on the distal treatment section. In addition, the jaw includes a second non-contact portion which is disposed to face the distal treatment section on a second jaw width direction side with respect to the abutment portion, and which has a space between it and the distal treatment section in the state where the abutment portion abuts on the distal treatment section. In the first non-contact portion, there is provided a first distance changing portion which forms an edge of the first non-contact portion on the first jaw width direction side, and in which a distance from the distal treatment section in a jaw opening direction changes along the jaw axis. Additionally, in the second non-contact portion, there is provided a second distance changing portion which forms an edge of the second non-contact portion on the second jaw width direction side, and in which a distance from the distal treatment section in the jaw opening direction changes along the jaw axis. In the state where the grasp object is grasped between the distal treatment section and the jaw, a movement of the grasp object along the jaw axis (the longitudinal axis) is regulated by the first distance changing portion and the second distance changing portion.

BRIEF SUMMARY OF THE INVENTION

According to one aspect of the invention, a grasping treatment device includes that: a probe which includes a distal treatment section in a distal portion thereof; a jaw which has a jaw axis and which is openable and closable relative to the distal treatment section; an abutment portion which is disposed in the jaw, and which is configured to abut on the distal treatment section by closing the jaw relative to the distal treatment section; a first non-contact portion which includes a first wall surface portion inclined so that the first wall surface portion is extended toward a distal treatment section side as the first wall surface portion is extended away from the abutment portion in the jaw, and which has a space between the first non-contact portion and the distal treatment section in a state where the abutment portion abuts on the distal treatment section; a continuous surface which forms an edge of the first non-contact portion, and which is shaped in a form of one surface continuous along a jaw axis direction parallel to the jaw axis; and a movement regulating portion which is provided in a region of the first non-contact portion located closer to the abutment portion than the continuous surface, which is configured to regulate a movement of a grasp object along the jaw axis direction in a state where the grasp object is grasped between the jaw closed relative to the distal treatment section and the distal treatment section, and which is formed in the first wall surface portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a schematic view showing a configuration of a distal portion of the grasping treatment device according to the first embodiment;

FIG. 5 is a perspective view schematically showing the configuration of the distal portion of the grasping treatment device according to the first embodiment;

FIG. 12 is a cross-sectional view schematically showing a first continuous surface of the jaw according to the first embodiment in a cross section perpendicular to a first jaw width direction and a second jaw width direction;

FIG. 13 is a perspective view schematically showing a configuration of a first non-contact portion and a second non-contact portion of the jaw according to the first embodiment;

FIG. 14 is a cross-sectional view schematically showing a first distance changing portion in a state where a grasp object is grasped between the jaw and the distal treatment section according to the first embodiment, in a cross section perpendicular to a jaw opening-and-closing direction;

FIG. 15 is a schematic view showing a certain example of a treatment of the grasp object by the grasping treatment device according to the first embodiment;

FIG. 16 is a schematic view showing another example of the treatment of the grasp object by the grasping treatment device according to the first embodiment, different from the example of FIG. 15;

FIG. 17 is a schematic view showing still another example of the treatment of the grasp object by the grasping treatment device according to the first embodiment, different from the examples of FIG. 15 and FIG. 16;

FIG. 18 is a cross-sectional view schematically showing a first continuous surface of a jaw according to a first modification in a cross section perpendicular to a first jaw width direction and a second jaw width direction;

FIG. 19 is a perspective view schematically showing a part of a jaw according to a second modification;

FIG. 20 is a perspective view schematically showing a configuration of a first non-contact portion and a second non-contact portion of a jaw according to a third modification;

DETAILED DESCRIPTION OF THE INVENTION

First Embodiment

A first embodiment of the present invention will be described with reference to FIG. 1 to FIG. 17.

Figure 1:
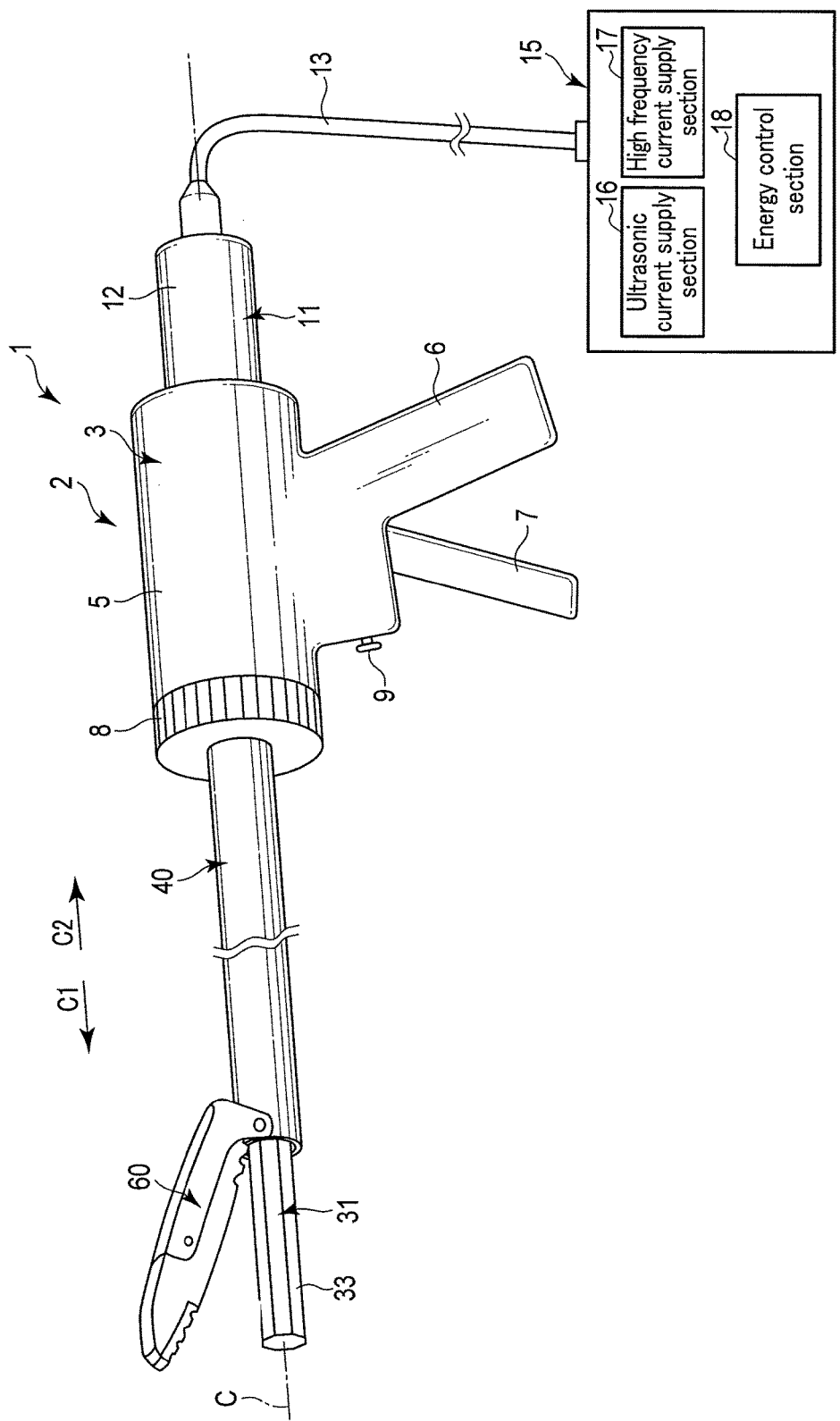
FIG. 1 is a schematic view showing a configuration of a grasping treatment system in which a grasping treatment device according to a first embodiment is used.

FIG. 1 is a view showing a configuration of a grasping treatment system 1 in which a grasping treatment device 2 of the present embodiment is used. As shown in FIG. 1, the grasping treatment device (a hand piece) 2 has a longitudinal axis C. Here, one of directions parallel to the longitudinal axis C is a distal direction (a direction of an arrow C1 of FIG. 1), and an opposite direction to the distal direction is a proximal direction (a direction of an arrow C2 of FIG. 1). Further, the distal direction and the proximal direction are defined as longitudinal axis directions. The grasping treatment device 2 is an ultrasonic treatment device configured to perform a treatment of a grasp object such as a biological tissue by use of an ultrasonic vibration. In addition, the grasping treatment device 2 is a high frequency treatment device (a bipolar treatment device) configured to perform the treatment of the grasp object by use of a high frequency current.

The grasping treatment device 2 includes a holding unit 3. The holding unit 3 includes a cylindrical case portion 5 extended along the longitudinal axis C, a fixed handle 6 formed integrally with the cylindrical case portion 5, and a movable handle 7 attached to the cylindrical case portion 5 to be turnable relative to the cylindrical case portion. When the movable handle 7 pivots around a position where the movable handle is attached to the cylindrical case portion 5, the movable handle 7 performs an opening-or-closing motion relative to the fixed handle 6. In addition, the holding unit 3 includes a rotary operation knob 8 attached to the distal direction side of the cylindrical case portion 5. The rotary operation knob 8 is rotatable relative to the cylindrical case member 5 around the longitudinal axis C. Additionally, in the fixed handle 6, there is disposed an energy operation input button 9 that is an energy operation input section.

The grasping treatment device 2 includes a vibrator unit 11. The vibrator unit 11 includes a vibrator case 12. The vibrator case 12 is rotatable relative to the cylindrical case portion 5 around the longitudinal axis C, integrally with the rotary operation knob 8. By inserting the vibrator case 12 from a proximal direction side into the cylindrical case portion 5, the vibrator case 12 is attached to the holding unit 3. To the vibrator case 12, one end of a cable 13 is connected.

The grasping treatment system 1 includes a control unit 15. The other end of the cable 13 is connected to the control unit 15. The control unit 15 includes an ultrasonic current supply section 16, a high frequency current supply section 17, and an energy control section 18. Here, the control unit 15 is an energy generator including a CPU (Central Processing Unit), an ASIC (Application Specific Integrated Circuit) and the like. In addition, the ultrasonic current supply section 16 and the high frequency current supply section 17 are power sources disposed in, e.g., the energy generator, and the energy control section 18 is formed from an electronic circuit (a control circuit) disposed in, e.g., the CPU, the ASIC or the like.

Figure 2:
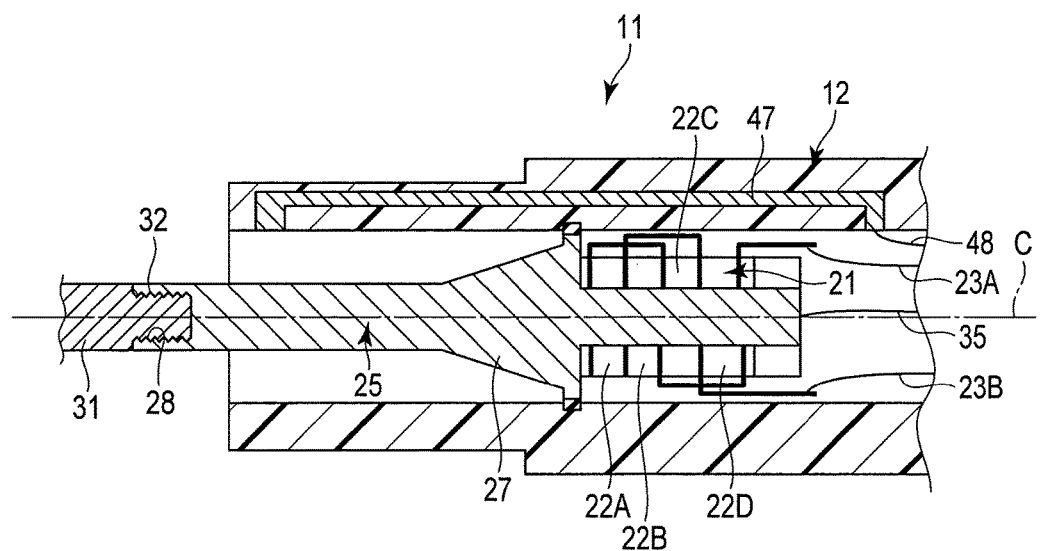
FIG. 2 is a cross-sectional view schematically showing a configuration of a vibrator unit according to the first embodiment.

FIG. 2 is a view showing a configuration of the vibrator unit 11. As shown in FIG. 2, the vibrator unit includes an ultrasonic vibrator 21 that is a vibration generating section provided in the vibrator case 12. The ultrasonic vibrator 21 includes a plurality of (four in the present embodiment) piezoelectric elements 22A to 22D configured to convert the current to the ultrasonic vibration. To the ultrasonic vibrator 21, one end of each of electric wires 23A and 23B is connected. The respective electric wires 23A and 23B are extended through an inside of the cable 13, and the other ends of the respective electric wires 23A and 23B are connected to the ultrasonic current supply section 16 of the control unit 15. When the current is supplied to the ultrasonic oscillator 21 from the ultrasonic current supply section 16 via the electric wires 23A and 23B, the ultrasonic vibration is generated in the ultrasonic vibrator 21.

The ultrasonic vibrator 21 is attached to a columnar horn member 25. The horn member 25 includes a sectional area changing portion 27 in which a sectional area perpendicular to the longitudinal axis C changes. The ultrasonic vibration generated in the ultrasonic vibrator 21 is transmitted to the horn member 25, and in the horn member 25, the ultrasonic vibration is transmitted from the proximal direction toward the distal direction. An amplitude of the ultrasonic vibration transmitted to the horn member 25 is enlarged in the sectional area changing portion 27. Additionally, in a distal portion of the horn member 25, an internal thread portion 28 is provided.

The grasping treatment device 2 includes a columnar probe 31 extended from the inside of the cylindrical case portion 5 toward the distal direction along the longitudinal axis C. In a proximal portion of the probe 31, an external thread portion 32 is disposed. By screwing the external thread portion 32 into the internal thread portion 28, the probe 31 is connected to a distal direction side of the horn member 25. The probe 31 is connected to the horn member 25 inside the cylindrical case member 5. The ultrasonic vibrator 21, the horn member 25 and the probe 31 are rotatable relative to the cylindrical case portion 5 around the longitudinal axis C, together with the rotary operation knob 8.

In the state where the probe 31 is connected to the horn member 25, the ultrasonic vibration is transmitted from the horn member 25 to the probe 31. Further, in the probe 31, the ultrasonic vibration is transmitted from the proximal direction toward the distal direction along the longitudinal axis C. At a distal portion of the probe 31, a distal treatment section 33 is disposed. In the probe 31, the ultrasonic vibration is transmitted to the distal treatment section 33. It is to be noted that the distal end of the probe 31 and a proximal end of the horn member 25 become antinode positions of the ultrasonic vibration. In addition, the ultrasonic vibration is a longitudinal vibration in which a vibrating direction and a transmitting direction are parallel to the longitudinal axis C.

To the horn member 25, one end of an electric wire 35 is connected. The electric wire 35 is extended through the inside of the cable 13, and the other end of the electric wire 35 is connected to the high frequency current supply section 17 of the control unit 15. Consequently, a probe side current path of the high frequency current to be supplied from the high frequency current supply section 17 is formed from the high frequency current supply section 17 through the electric wire 35, the horn member 25 and the probe 31 to the distal treatment section 33. When the high frequency current (high frequency energy) is supplied to the distal treatment section 33 via the probe side current path, the distal treatment section 33 functions as a probe electrode portion having a first potential E1.

The grasping treatment device 2 includes a sheath 40 extended along the longitudinal axis C. By inserting the sheath 40 from the distal direction side into the rotary operation knob 8 and the cylindrical case portion 5, the sheath 40 is attached to the holding unit 3. Inside the cylindrical case portion 5, the sheath 40 is attached to the distal direction side of the vibrator case 12.

Figure 3:
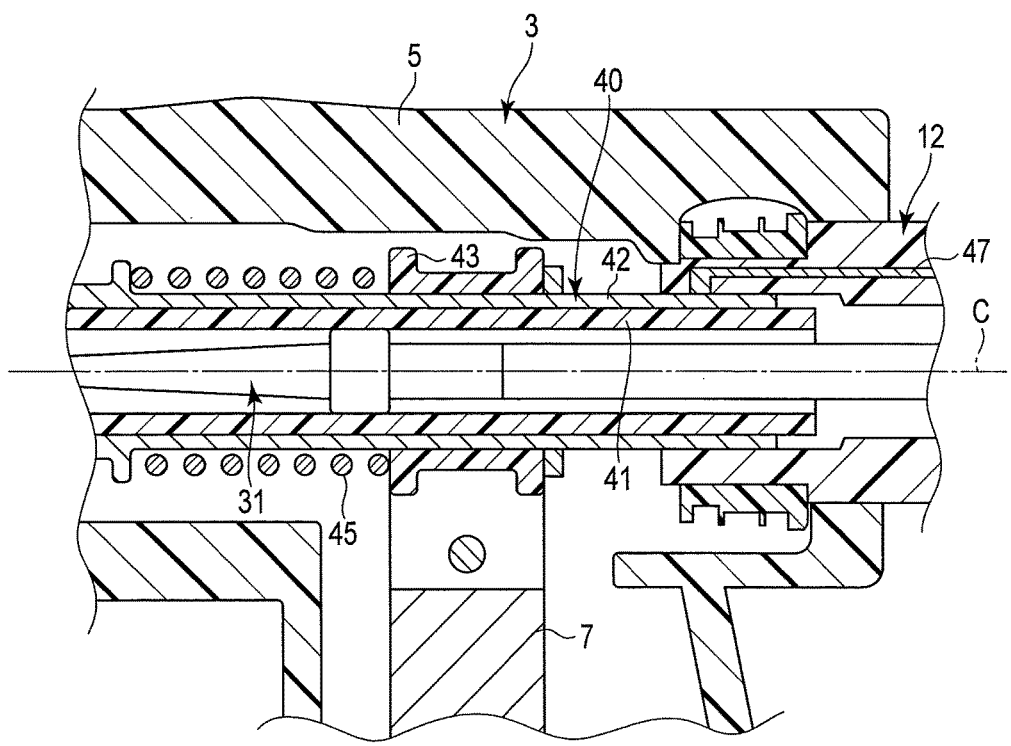
FIG. 3 is a cross-sectional view schematically showing an inner configuration of a cylindrical case portion of a holding unit according to the first embodiment.

FIG. 3 is a view showing an internal configuration of the cylindrical case portion 5 of the holding unit 3. As shown in FIG. 3, the sheath 40 includes a connection cylindrical portion 41 made of an insulating material, and a movable cylindrical portion 42 provided on an outer peripheral direction side with respect to the connection cylindrical portion 41. The movable cylindrical portion 42 is made of a conductive material, and is movable relative to the vibrator case 12 and the connection cylindrical portion 41 along the longitudinal axis C. In an outer peripheral portion of the movable cylindrical portion 42, a slider member 43 made of an insulating material is provided. The slider member 43 is movable relative to the movable cylindrical portion 42 along the longitudinal axis C. The slider member 43 is connected to the movable cylindrical portion 42 via an elastic member 45 such as a coil spring. In addition, the movable handle 7 is attached to the slider member 43. When the movable handle 7 is opened or closed relative to the fixed handle 6, a drive force is transmitted to the slider member 43, and the slider member 43 moves along the longitudinal axis C. Further, the drive force is transmitted from the slider member 43 to the movable cylindrical portion 42 via the elastic member 45, and the movable cylindrical portion 42 moves to the vibrator case 12 and the connection cylindrical portion 41 along the longitudinal axis C.

As shown in FIG. 2 and FIG. 3, a conductive portion 47 is formed in the vibrator case 12. To the conductive portion 47, one end of an electric wire 48 is connected. The electric wire 48 is extended through the inside of the cable 13, and the other end of the electric wire 48 is connected to the high frequency current supply section 17 of the control unit 15. Further, in a state where the sheath 40 is connected to the vibrator case 12, the movable cylindrical portion 42 of the sheath 40 movably abuts on the conductive portion 47 of the oscillator case 12. Consequently, in the state where the sheath 40 is connected to the vibrator case 12, the vibrator case 12 is electrically connected to the movable cylindrical portion 42. In consequence, the high frequency current is supplied from the high frequency current supply section 17 to the movable cylindrical portion 42 of the sheath 40 through the electric wire 48 and the conductive portion 47 of the vibrator case 12. It is to be noted that the conductive portion 47 of the vibrator case 12 and the movable cylindrical portion 42 of the sheath 40 are electrically insulated from the horn member 25 and the probe 31.

The energy control section 18 is configured to control a supply state of a generating-ultrasonic current from the ultrasonic current supply section 16 and a supply state of the high frequency current from the high frequency current supply section 17, on the basis of an input of an energy operation with the energy operation input button 9. Inside the fixed handle 6, a switch (not shown) is provided. When the energy operation input button 9 is pressed and the energy operation is input, the switch is closed. The switch is electrically connected to the energy control section 18. When the switch is closed, an electric signal is transmitted to the energy control section 18, and the input of the energy operation is detected. When the input of the energy operation is detected, the generating-ultrasonic current is supplied from the ultrasonic current supply section 16, and the high frequency current is supplied from the high frequency current supply section 17.

FIG. 4 and FIG. 5 are views showing a configuration of a distal portion of the grasping treatment device 2. As shown in FIG. 4, the sheath 40 includes an inner tube 51 made of an insulating material, a movable pipe 52 provided on an outer peripheral direction side with respect to the inner tube 51, and an outer tube 53 disposed on an outer peripheral direction side with respect to the movable pipe 52. The movable pipe 52 is made of a conductive material and the outer tube 53 is made of an insulating material. A proximal portion of the movable pipe 52 is coupled with a distal portion of the movable cylindrical portion 42. When the drive force is transmitted to the movable pipe 52 by the closing motion of the movable handle 7 relative to the fixed handle 6, the movable pipe 52 moves relative to the inner tube 51 and the outer tube 53 along the longitudinal axis C, integrally with the movable cylindrical portion 42. In addition, the high frequency current transmitted from the high frequency current supply section 17 to the movable cylindrical portion 42 is transmitted to the movable pipe 52.

As shown in FIG. 4 and FIG. 5, a proximal portion of a jaw 60 that is a grasping unit is attached to a distal portion of the outer tube 53 of the sheath 40 via a coupling screw 55. The jaw 60 is extended along a jaw axis J. The jaw 60 pivots relative to the sheath 40 around the coupling screw 55. A pivoting axis P of the jaw 60 is perpendicular to the longitudinal axis C and the jaw axis J. In addition, a distal portion of the movable pipe 52 is connected to the jaw 60. The high frequency current is transmitted from the movable pipe 52 to the jaw 60. As described above, a jaw side current path is formed from the high frequency current supply section 17 to the jaw 60 through the electric wire 48, the conductive portion 47 of the vibrator case 12, the movable cylindrical portion 42, and the movable pipe 52. The high frequency current (the high frequency energy) is transmitted from the high frequency current supply section 17 to the jaw 60 through the jaw side current path.

When the movable cylindrical portion 42 and the movable pipe 52 move together along the longitudinal axis C, the drive force is transmitted from the movable pipe 52 to the jaw 60, and the jaw 60 turns around on the pivoting axis P. In consequence, the jaw 60 performs the opening-or-closing motion relative to the distal treatment section 33 of the probe 31. Consequently, in a state where the jaw 60 is closed relative to the distal treatment section 33, a grasp target such as the biological tissue can be grasped between the jaw 60 and the distal treatment section 33. It is to be noted that a jaw opening-or-closing direction of the jaw 60 is perpendicular to the longitudinal axis C and the jaw axis J. Here, a direction of the jaw 60 toward the distal treatment section 33 is the jaw closing direction (a direction of an arrow A1 of FIG. 4 and FIG. 5), and a direction of the jaw 60 away from the distal treatment section 33 is the jaw opening direction (a direction of an arrow A2 of FIG. 4 and FIG. 5). In the state where the jaw 60 is closed relative to the distal treatment section 33, the jaw axis J is substantially parallel to the longitudinal axis C. In addition, the turning axis P of the jaw 60 is perpendicular to the jaw opening-or-closing direction. It is to be noted that FIG. 4 and FIG. 5 show a state where the jaw 60 is opened relative to the distal treatment section 33.

The jaw 60 includes a jaw main body 61 attached to the sheath 40, and a jaw conductive member 62 attached to the jaw main body 61 via a connecting screw 59. The jaw main body 61 is made of a conductive material. The high frequency current transmitted from the movable pipe 52 of the sheath 40 to the jaw 60 is transmitted to the jaw conductive member 62 through the jaw main body 61. When the high frequency current is transmitted to the jaw conductive member 62, the jaw conductive member 62 functions as a jaw electrode portion having a second potential E2 that is a potential different from the first potential E1 of the probe electrode portion (33). In addition, a jaw insulating member 63 made of an insulating material is attached to the jaw conductive member 62.

Figure 6:
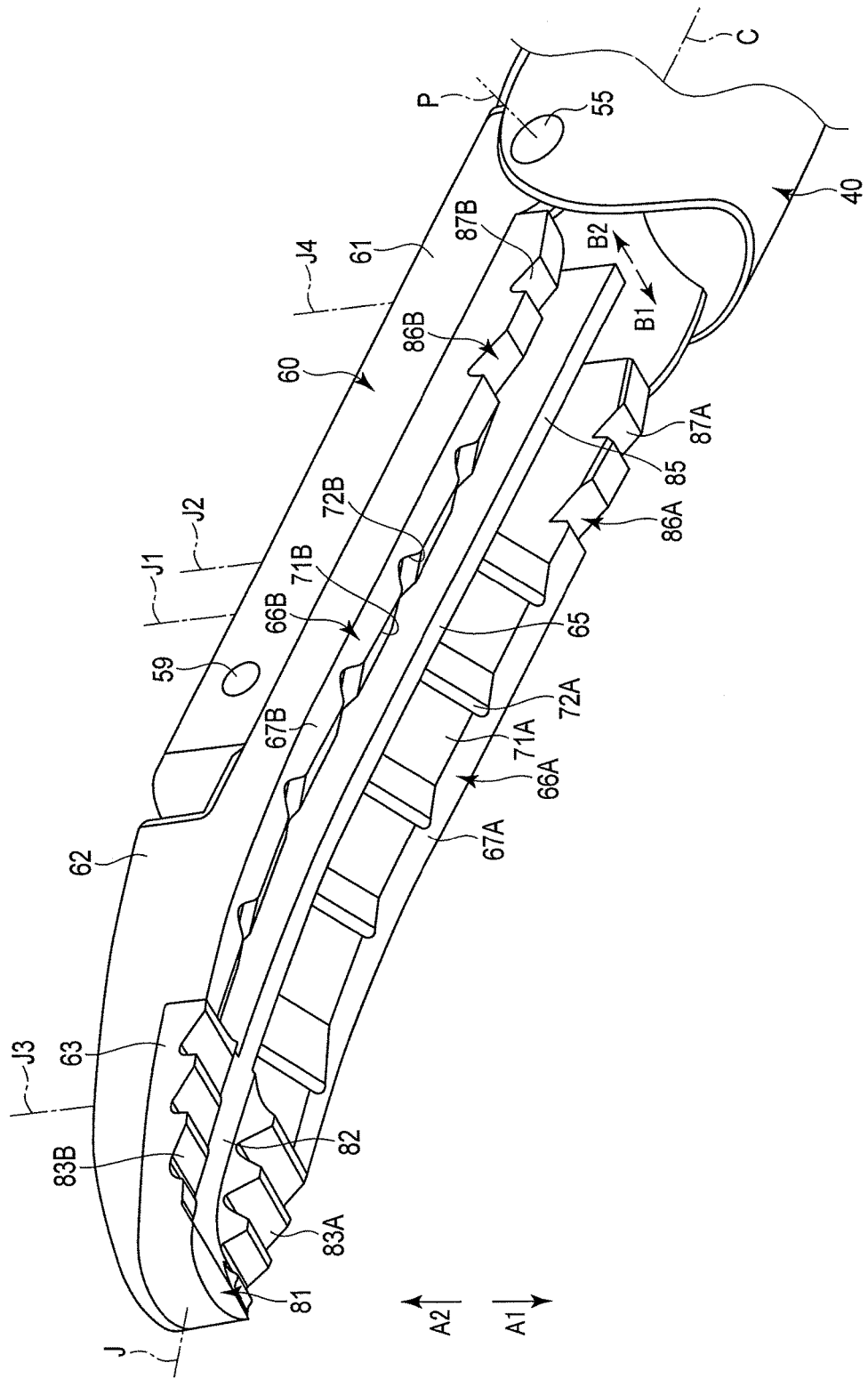
FIG. 6 is a perspective view schematically showing a configuration of a distal portion of a sheath and a jaw according to the first embodiment.
Figure 7:
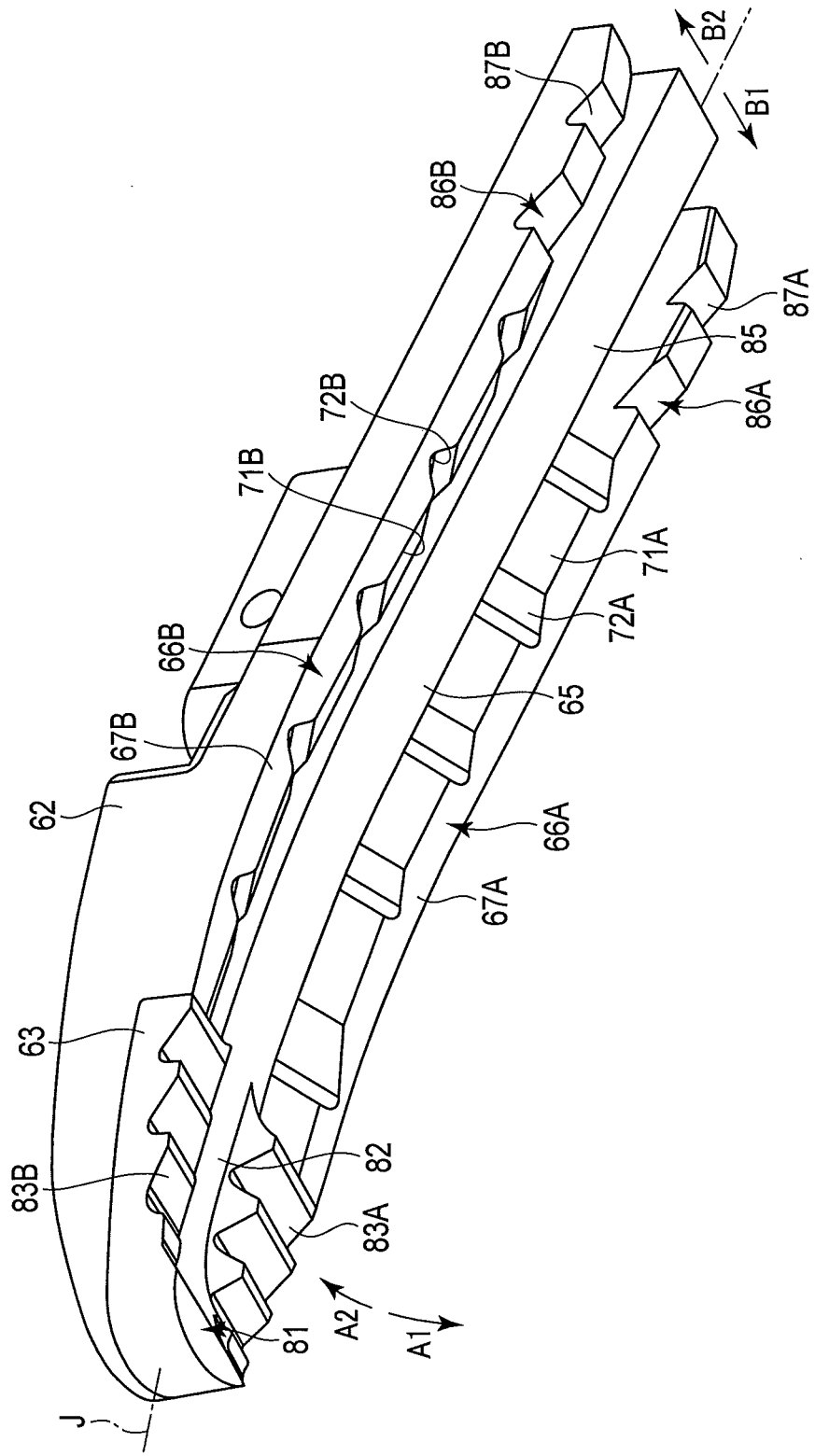
FIG. 7 is a perspective view schematically showing a configuration of a jaw conductive member and a jaw insulating member of the jaw according to the first embodiment.
Figure 8:
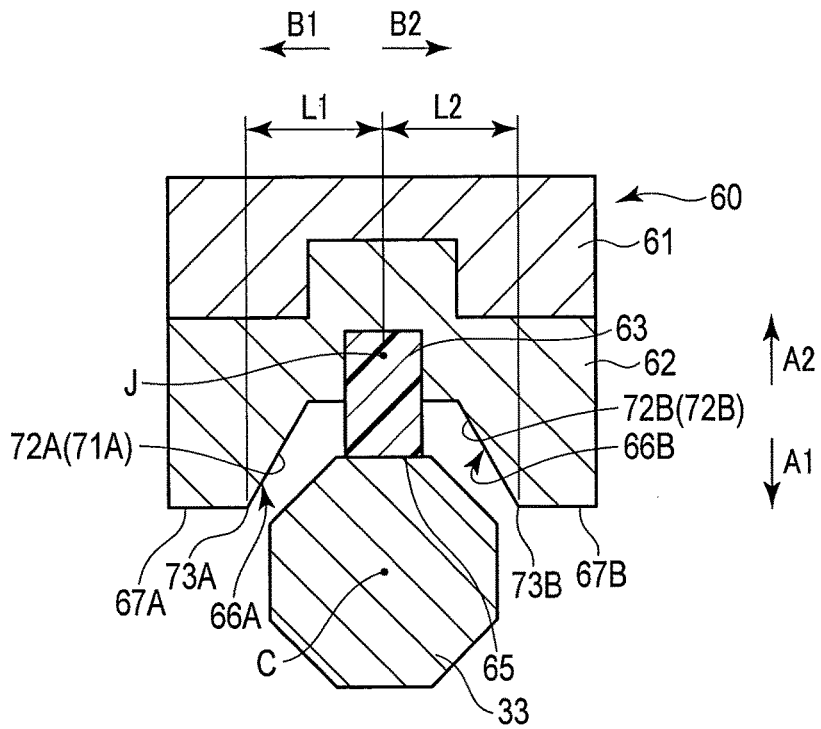
FIG. 8 is a cross-sectional view schematically showing the jaw and a distal treatment section according to the first embodiment in a given cross section perpendicular to a jaw axis and a longitudinal axis.
Figure 9:
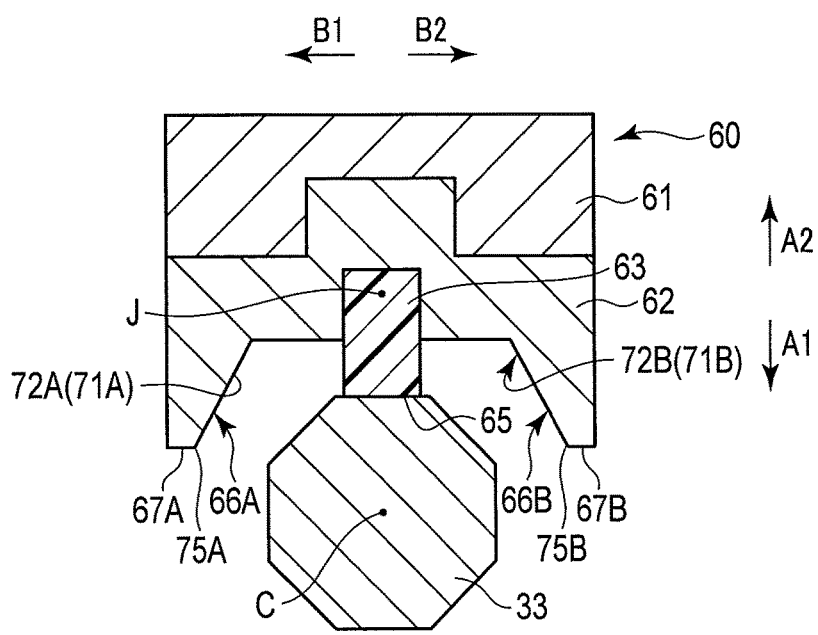
FIG. 9 is a cross-sectional view schematically showing the jaw and the distal treatment section according to the first embodiment in a given cross section that is perpendicular to the jaw axis and the longitudinal axis and is different from that of FIG. 8.
Figure 10:
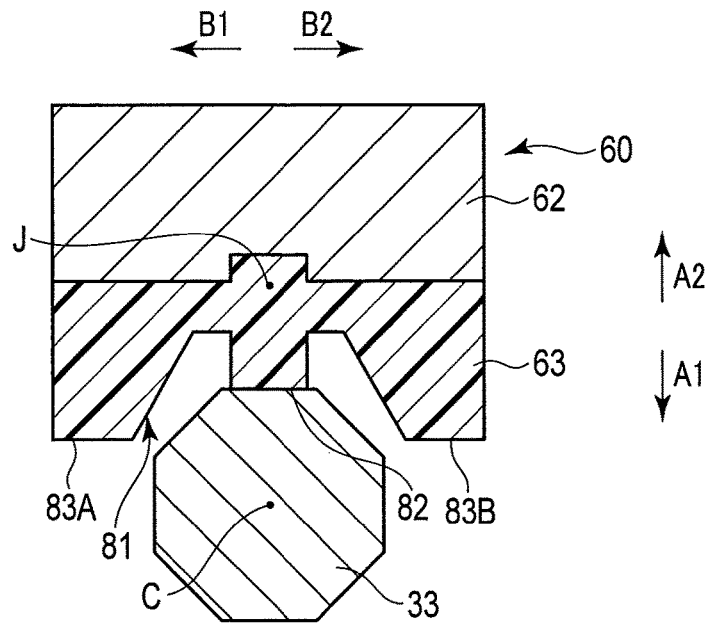
FIG. 10 is a cross-sectional view schematically showing the jaw and the distal treatment section according to the first embodiment in a given cross section that is perpendicular to the jaw axis and the longitudinal axis and is different from those of FIG. 8 and FIG. 9.
Figure 11:
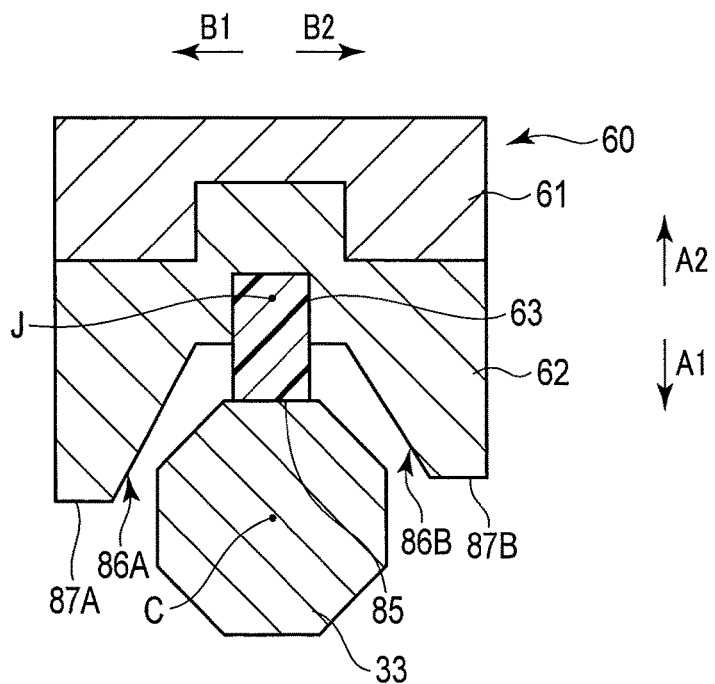
FIG. 11 is a cross-sectional view schematically showing the jaw and the distal treatment end according to the first embodiment in a given cross section that is perpendicular to the jaw axis and the longitudinal axis and is different from those of FIG. 8 to FIG. 10.

FIG. 6 is a view showing a configuration of a distal portion of the sheath 40 and the jaw 60. FIG. 7 is a view showing a configuration of the jaw conductive member 62 and the jaw insulating member 63 of the jaw 60. Further, each of FIG. 8 to FIG. 11 is a view showing the jaw 60 and the distal treatment section 33 in a cross section perpendicular to the jaw axis J and the longitudinal axis C. FIG. 8 to FIG. 11 show the state that the jaw 60 is closed relative to the distal treatment section 33. The cross section shown in FIG. 8 is a cross section passing a position J1 of FIG. 6 in a jaw axis direction parallel to the jaw axis J. The cross section shown in FIG. 9 is a cross section passing a position J2 of FIG. 6 in the jaw axis direction. Further, the cross section shown in FIG. 10 is a cross section passing a position J3 of FIG. 6 in the jaw axis direction, and the cross section shown in FIG. 11 is a cross section passing a position J4 of FIG. 6 in the jaw axis direction. It is to be noted that, in FIG. 8 to FIG. 11, the jaw insulating member 63 of the jaw 60 abuts on the distal treatment section 33.

As shown in FIG. 5 to FIG. 9, the jaw insulating member 63 includes an abutment portion 65 that can abut on the distal treatment section 33 in the state where the jaw 60 is closed relative to the distal treatment section 33. When the jaw 60 is closed relative to the distal treatment section 33 in a state where no grasp object is interposed between the jaw 60 and the distal treatment section 33, the abutment portion 65 abuts on the distal treatment section 33. The abutment portion 65 faces toward the jaw closing direction (the direction of the arrow A1 of FIG. 5 to FIG. 9) to face the distal treatment section 33. Here, directions that are perpendicular to the longitudinal axis C and the jaw axis J and perpendicular to the jaw opening-or-closing direction are defined as a first jaw width direction (a direction of an arrow B1 of FIG. 5 to FIG. 9) and a second jaw width direction (a direction of an arrow B2 of FIG. 5 to FIG. 9). The first jaw width direction is an opposite direction relative to the second jaw width direction. In addition, the first jaw width direction and the second jaw width direction are parallel to the pivoting axis P of the jaw 60.

The jaw conductive member 62 includes a first non-contact portion 66A and a second non-contact portion 66B each having a space between it and the distal treatment section 33 in a state where the abutment portion 65 abuts on the distal treatment section 33. The first non-contact portion 66A and the second non-contact portion 66B are provided to face the distal treatment section 33. The first non-contact portion 66A and the second non-contact portion 66B do not come in contact with the distal treatment section 33, and hence the jaw conductive member (the jaw electrode portion) 62 does not come in contact with the distal treatment section (the probe electrode portion) 33. The first non-contact portion 66A and the second non-contact portion 66B are extended over the same region as in the abutment portion 65 in the jaw axis direction parallel to the jaw axis J. The first non-contact portion 66A is positioned on a first jaw width direction side with respect to the abutment portion 65, and the second non-contact portion 66B is positioned on a second jaw width direction side with respect to the abutment portion 65.

The first non-contact portion 66A includes a first continuous surface 67A shaped in the form of one surface that is continuous along the jaw axis J. The first continuous surface 67A forms an edge of the first non-contact portion 66A on the first jaw width direction side. FIG. 12 is a view showing the first continuous surface 67A in a cross section perpendicular to the first jaw width direction and the second jaw width direction. As shown in FIG. 12, the first continuous surface 67A is a curved surface having a curved line shape with a large bending radius R1 in the cross section perpendicular to the first jaw width direction and the second jaw width direction. The first continuous surface 67A is one continuous surface, and hence in the first continuous surface 67A, a narrowing sharp portion is not formed. The first continuous surface 67A is formed in such a shape as described above, and hence in a state where the grasp object is interposed between the jaw 60 opened relative to the distal treatment section 33 and the distal treatment section 33, a movement of the grasp object along the jaw axis J is not regulated by the first continuous surface 67A. However, when the bending radius R1 of the first continuous surface 67A in the cross section perpendicular to the first jaw width direction and the second jaw width direction becomes smaller, there is the possibility that the movement of the grasp object along the jaw axis J is regulated by the first continuous surface 67A in the state where the grasp object is interposed between the jaw 60 opened relative to the distal treatment section 33 and the distal treatment section 33. Therefore, it is necessary to increase the bending radius R1 of the first continuous surface 67A in the cross section perpendicular to the first jaw width direction and the second jaw width direction to such an extent that the movement of the grasp object along the jaw axis J is not regulated.

The second non-contact portion 66B includes a second continuous surface 67B shaped in the form of one surface that is continuous along the jaw axis J. The second continuous surface 67B forms an edge of the second non-contact portion 66B on the second jaw width direction side. The second continuous surface 67B is formed into a shape similar to that of the first continuous surface 67A. That is, the second continuous surface 67B is a curved surface having a curved line shape with a large bending radius R2 in the cross section perpendicular to the first jaw width direction and the second jaw width direction. Consequently, in the state where the grasp target is interposed between the jaw 60 opened relative to the distal treatment section 33 and the distal treatment section 33, the movement of the grasp object along the jaw axis J is not regulated by the second continuous surface 67B. Here, the bending radius R2 of the second continuous surface 67B in the cross section perpendicular to the first jaw width direction and the second jaw width direction is large to such an extent that the movement of the grasp object along the jaw axis J is not regulated.

FIG. 13 is a view showing a configuration of the first non-contact portion 66A and the second non-contact portion 66B. It is to be noted that the jaw insulating member 63 (the abutment portion 65) is omitted from FIG. 13. As shown in FIG. 8, FIG. 9 and FIG. 13, the first non-contact portion 66A includes a first wall surface portion 71A facing toward the second jaw width direction (the direction of the arrow B2 of FIG. 13). The first wall surface portion 71A is located on the second jaw width direction side with respect to the first continuous surface 67A. That is, the first wall surface portion 71A is disposed between the abutment portion 65 and the first continuous surface 67A. In addition, the second non-contact portion 66B includes a second wall surface portion 71B facing toward the first jaw width direction (the direction of the arrow B1 of FIG. 13). The second wall surface portion 71B is located on the first jaw width direction side with respect to the second continuous surface 67B. That is, the second wall surface portion 71B is disposed between the abutment portion 65 and the second continuous surface 67B.

In the first wall surface portion 71A, a first distance changing portion 72A, in which a distance from the jaw axis J in the first jaw width direction changes along the jaw axis J, is provided. The first distance changing portion 72A includes a first reference surface 73A positioned at a first reference distance L1 from the jaw axis J in the first jaw width direction. In addition, the first distance changing portion 72A includes first concave portions 75A concaved from the first reference surface 73A toward the first jaw width direction. In each of the first concave portions 75A, the distance from the jaw axis J in the first jaw width direction is larger than the first reference distance L1. An end of each of the first concave portions 75A on the first jaw width direction side is formed in a narrowing manner to be sharp. The first distance changing portion 72A is formed in a convex-and-concave manner by the first reference surface 73A and the first concave portions 75A.

Due to the abovementioned configuration, in the first distance changing portion 72A, the movement of the grasp object along the jaw axis J is regulated in a state where the grasp object is grasped between the jaw 60 closed relative to the distal treatment section 33 and the distal treatment section 33. That is, the first distance changing portion 72A is a movement regulating portion configured to regulate the movement of the grasp object along the jaw axis J in the state where the grasp object is grasped between the jaw 60 closed relative to the distal treatment section 33 and the distal treatment section 33. In addition, the first distance changing portion 72A is positioned in the first wall surface portion 71A that is located on the second jaw width direction side with respect to the first continuous surface 67A to face toward the second jaw width direction. Consequently, in the state where the grasp target is interposed between the jaw 60 opened relative to the distal treatment section 33 and the distal treatment section 33, the grasp object does not come in contact with the first distance changing portion 72A (the first wall surface portion 71A).

FIG. 14 is a view showing the first distance changing portion 72A in the state where a grasp object S is grasped between the jaw 60 and the distal treatment section 33, in the cross section perpendicular to the jaw opening and closing directions (the direction of the arrow A1 and the direction of the arrow A2 of FIG. 13). As shown in FIG. 14, in the state where the grasp object S is grasped between the jaw 60 and the distal treatment section 33, the whole first distance changing portion 72A does not come in contact with the grasp object S, but the first distance changing portion 72A partially comes in contact with the grasp object S. That is, the first distance changing portion 72A is formed into such a shape to partially come in contact with the grasp object S in the state where the grasp object S is grasped between the jaw 60 closed relative to the distal treatment section 33 and the distal treatment section 33. In a part of the first distance changing portion 72A which does not come in contact with the grasp object S, a space is present between the first distance changing portion 72A and the grasp object S. The first distance changing portion 72A partially comes in contact with the grasp object S, and hence a contact area between the first non-contact portion 66A that is a part of the jaw electrode portion (62) and the biological tissue decreases.

Additionally, in the second wall surface portion 71B, a second distance changing portion 72B, in which a distance from the jaw axis J in the second jaw width direction changes along the jaw axis J, is provided. The second distance changing portion 72B includes a second reference surface 73B positioned at a second reference distance L2 from the jaw axis J in the second jaw width direction. In addition, the second distance changing portion 72B includes second concave portions 75B concaved from the second reference surface 73B toward the second jaw width direction. In each of the second concave portions 75B, the distance from the jaw axis J in the second jaw width direction is larger than the second reference distance L2. An end of each of the second concave portions 75B on the second jaw width direction side is formed in a narrowing manner to be sharp. The second distance changing portion 72B is formed in a convex-and-concave manner by the second reference surface 73B and the second concave portions 75B.

Due to the abovementioned configuration, similarly to the first distance changing portion 72A, the second distance changing portion 72B is a movement regulating portion configured to regulate the movement of the grasp object along the jaw axis J in the state where the grasp object is grasped between the jaw 60 closed relative to the distal treatment section 33 and the distal treatment section 33. In addition, the second distance changing portion 72B is positioned in the second wall surface portion 71B that is located on the first jaw width direction side with respect to the second continuous surface 67B to face toward the first jaw width direction. Consequently, in the state where the grasp object is interposed between the jaw 60 opened relative to the distal treatment section 33 and the distal treatment section 33, the grasp object does not come in contact with the second distance changing portion 72B (the second wall surface portion 71B). Furthermore, similarly to the first distance changing portion 72A, the whole second distance changing portion 72B does not come in contact with the grasp object S, and the second distance changing portion 72B partially comes in contact with the grasp object S in the state where the grasp object S is grasped between the jaw 60 and the distal treatment section 33. The second distance changing portion 72B partially comes in contact with the grasp object S, and hence a contact area between the second non-contact portion 66B that is a part of the jaw electrode portion (62) and the biological tissue decreases.

It is to be noted that the cross section shown in FIG. 8 is a cross section passing the first reference surface 73A of the first distance changing portion 72A and the second reference surface 73B of the second distance changing portion 72B. In addition, the cross section shown in FIG. 9 is a cross section passing one of the first concave portions 75A of the first distance changing portion 72A and one of the second concave portions 75B of the second distance changing portion 72B.

As shown in FIG. 5 to FIG. 7 and FIG. 10, in the jaw 60, an entire width insulating portion 81, in which the jaw insulating member 63 is extended over an entire width of the jaw 60 from the edge of the jaw on the first jaw width direction side to the edge of the jaw on the second jaw width direction side, is provided. The entire width insulating portion 81 is made of an insulating material such as Teflon (registered trademark) along the whole width of the jaw 60 from the edge of the jaw on the first jaw width direction side to the edge of the jaw on the second jaw width direction side. The entire width insulating portion 81 is extended along the jaw axis J on a distal direction side with respect to the abutment portion 65, the first non-contact portion 66A and the second non-contact portion 66B. Therefore, the entire width insulating portion 81 is positioned in a distal portion of the jaw 60. In addition, the entire width insulating portion 81 faces the distal treatment section 33. It is to be noted that the cross section shown in FIG. 10 is a cross section passing the entire width insulating portion 81.

The entire width insulating portion 81 includes a distal side abutment portion 82 that can abut on the distal treatment section 33 in the state where the jaw 60 is closed relative to the distal treatment section 33. The distal side abutment portion 82 is continuously provided on the distal direction side of the abutment portion 65. When the jaw 60 is closed in the state where the grasp object is not interposed between the jaw 60 and the distal treatment section 33, the distal side abutment portion 82 abuts on the distal treatment section 33. That is, in a state where the abutment portion 65 abuts on the distal treatment section 33, the distal side abutment portion 82 abuts on the distal treatment section 33.

In addition, the entire width insulating portion 81 includes a first distal side distance changing portion 83A and a second distal side distance changing portion 83B in each of which a distance from the distal treatment section 33 in the jaw opening direction (the direction of the arrow A2 of FIG. 5 to FIG. 7) changes along the jaw axis J. Each of the first distal side distance changing portion 83A and the second distal side distance changing portion 83B is shaped in the form of a convex-and-concave surface facing toward the jaw closing direction (the direction of the arrow A1 of FIG. 5 to FIG. 7). The first distal side distance changing portion 83A is positioned on the first jaw width direction side with respect to the distal side abutment portion 82, and forms an edge of the entire width insulating portion 81 on the first jaw width direction side. The second distal side distance changing portion 83B is positioned on the second jaw width direction side with respect to the distal side abutment portion 82, and forms an edge of the entire width insulating portion 81 on the second jaw width direction side. Each of the first distal side distance changing portion 83A and the second distal side distance changing portion 83B has a space between the it and the distal treatment section 33 in a state where the distal side abutment portion 82 abuts on the distal treatment section 33. The first distal side distance changing portion 83A and the second distal side distance changing portion 83B are formed into such shapes as described above, and hence in the state where the grasp object is grasped between the jaw 60 closed relative to the distal treatment section 33 and the distal treatment section 33, the movement of the grasp object along the jaw axis J is regulated by the first distal side distance changing portion 83A and the second distal side distance changing portion 83B.

In addition, the entire width insulating portion 81 is made of a material such as Teflon having high slipping properties, and hence in the entire width insulating portion 81, the slipping properties of the grasp object heighten as compared with the first non-contact portion 66A and the second non-contact portion 66B of the jaw conductive member 62 made of a metal. Consequently, in the state where the grasp object is interposed between the jaw 60 opened relative to the distal treatment section 33 and the distal treatment section 33, the movement of the grasp object along the jaw axis J is not regulated by the first distal side distance changing portion 83A and the second distal side distance changing portion 83B.

As shown in FIG. 5 to FIG. 7 and FIG. 11, the jaw insulating member 63 of the jaw 60 includes a proximal side abutment portion 85 provided on a proximal direction side with respect to the abutment portion 65. The proximal side abutment portion 85 is continuously extended on the proximal side of the abutment portion 65, and positioned in the proximal portion of the jaw 60. In the state where the jaw 60 is closed relative to the distal treatment section 33, the proximal side abutment portion 85 can abut on the distal treatment section 33. When the jaw 60 is closed in the state where the grasp object is not interposed between the jaw 60 and the distal treatment section 33, the proximal side abutment portion 85 abuts on the distal treatment section 33. That is, in the state where the abutment portion 65 abuts on the distal treatment section 33, the proximal side abutment portion 85 abuts on the distal treatment section 33. It is to be noted that the cross section in FIG. 11 is a cross section passing the proximal side abutment portion 85.

The jaw conductive member 62 includes a first proximal side non-contact portion 86A and a second proximal side non-contact portion 86B each having a space between it and the distal treatment section 33 in a state where the proximal side abutment portion 85 abuts on the distal treatment section 33. The first proximal side non-contact portion 86A and the second proximal side non-contact portion 86B are disposed to face the distal treatment section 33. The first proximal side non-contact portion 86A and the second proximal side non-contact portion 86B are provided over the same region as that of the proximal side abutment portion 85 in the jaw axis direction parallel to the jaw axis J. Consequently, the first proximal side non-contact portion 86A and the second proximal side non-contact portion 86B are positioned in the proximal portion of the jaw 60. The first proximal side non-contact portion 86A is positioned on the first jaw width direction side with respect to the proximal side abutment portion 85, and the second proximal side non-contact portion 86B is positioned on the second jaw width direction side with respect to the proximal side abutment portion 85. In addition, the first proximal side non-contact portion 86A is continuously extended on the proximal side of the first non-contact portion 66A, and the second proximal side non-contact portion 86B is continuously extended on the proximal side of the second non-contact portion 66B.

In the first proximal side non-contact portion 86A, a first proximal side distance changing portion 87A, in which a distance from the distal treatment section 33 in the jaw opening direction (the direction of the arrow A2 of FIG. 5 to FIG. 7) changes along the jaw axis J, is provided. Additionally, in the second proximal side non-contact portion 86B, a second proximal side distance changing portion 87B, in which the distance from the distal treatment section 33 in the jaw opening direction changes along the jaw axis J, is provided. Each of the first proximal side distance changing portion 87A and the second proximal side distance changing portion 87B is shaped in the form of a convex-and-concave surface facing in the jaw closing direction (the direction of the arrow A1 of FIG. 5 to FIG. 7). The first proximal side distance changing portion 87A forms an edge of the first proximal side non-contact portion 86A on the first jaw width direction side, and the second proximal side distance changing portion 87B forms an edge of the second proximal side non-contact portion 86B on the second jaw width direction side. Each of the first proximal side distance changing portion 87A and the second proximal side distance changing portion 87B is formed into such a shape as described above, and hence in the state where the grasp object is grasped between the jaw 60 closed relative to the distal treatment section 33 and the distal treatment section 33, the movement of the grasp object along the jaw axis J is regulated by the first proximal side distance changing portion 87A and the second proximal side distance changing portion 87B. It is to be noted that the first proximal side distance changing portion 87A and the second proximal side distance changing portion 87B are positioned in the proximal portion of the jaw 60, and hence in the state where the grasp object is interposed between the jaw 60 opened relative to the distal treatment section 33 and the distal treatment section 33, the grasp object does not come in contact with the first proximal side distance changing portion 87A and the second proximal side distance changing portion 87B.

Next, a function and an effect of the grasping treatment device 2 and the grasping treatment system 1 will be described. When a grasp object such as the biological tissue is treated by using the grasping treatment device 2, the probe 31, the sheath 40 and the jaw 60 are inserted into a body cavity, and the distal treatment section 33 and the jaw 60 are arranged in the vicinity of the grasp object. In this case, the jaw 60 is opened relative to the distal treatment section 33 of the probe 31. In this state, the grasp object is inserted from the distal direction side between the jaw 60 and the distal treatment section 33. Here, in the entire width insulating portion 81 including the first distal side distance changing portion 83A and the second distal side distance changing portion 83B, the slipping properties of the grasp object are high. Consequently, the movement of the grasp object along the jaw axis J is not regulated by the first distal side distance changing portion 83A and the second distal side distance changing portion 83B.

In addition, each of the first continuous surface 67A forming the end of the first non-contact portion 66A on the first jaw width direction side and the second continuous surface 67B forming the end of the second non-contact portion 66B on the second jaw width direction side is the curved surface having the curved line shape with the large bending radius (R1 or R2) in the cross section perpendicular to the first jaw width direction and the second jaw width direction. Consequently, when the grasp object is interposed between the jaw 60 opened relative to the distal treatment section 33 and the distal treatment section 33, the movement of the grasp object along the jaw axis J is not regulated by the first continuous surface 67A and the second continuous surface 67B. In addition, the first distance changing portion 72A is positioned in the first wall surface portion 71A that is located on the second jaw width direction side with respect to the first continuous surface 67A to face toward the second jaw width direction. Further, the second distance changing portion 72B is positioned in the second wall surface portion 71B that is located on the first jaw width direction side with respect to the second continuous surface 67B to face toward the first jaw width direction. Consequently, when the grasp object is interposed between the jaw 60 opened relative to the distal treatment section 33 and the distal treatment section 33, the grasp object does not come in contact with the first distance changing portion 72A (the first wall surface portion 71A) and the second distance changing portion 72B (the second wall surface portion 71B).

Furthermore, the first proximal side distance changing portion 87A and the second proximal side distance changing portion 87B are positioned in the proximal portion of the jaw. Consequently, when the grasp object is interposed between the jaw 60 opened relative to the distal treatment section 33 and the distal treatment section 33, the grasp object does not come in contact with the first proximal side distance changing portion 87A and the second proximal side distance changing portion 87B.

The grasp object is interposed between the jaw 60 and the distal treatment section 33 as described above, and hence the movement of the interposed grasp object along the jaw axis J is not regulated. Consequently, in the state where the grasp object is interposed between the jaw 60 opened relative to the distal treatment section 33 and the distal treatment section 33, the grasp object can effectively be prevented from being hitched on the jaw 60. In consequence, it is possible to effectively prevent deterioration of a treatment performance of the grasp object due to the hitching of the grasp object on the jaw 60.

In the state where the biological tissue is interposed between the jaw 60 and the distal treatment section 33, the movable handle 7 closes relative to the fixed handle 6. Consequently, the movable cylindrical portion 42 of the sheath 40 and the movable pipe 52 move along the longitudinal axis C, and the jaw 60 closes relative to the distal treatment section 33. Consequently, a grasp object such as the biological tissue is grasped between the jaw 60 and the distal treatment section 33.

Further, in the state where the grasp object is grasped between the jaw 60 and the distal treatment section 33, the energy operation is input with the energy operation input button 9. When the input of the energy operation is detected by the energy control section 18, the generating-ultrasonic current is supplied from the ultrasonic current supply section 16, and the high frequency current is supplied from the high frequency current supply section 17. The generating-ultrasonic current is supplied to the ultrasonic vibrator 21, thereby generating the ultrasonic vibration. The generated ultrasonic vibration is transmitted to the probe 31 through the horn member 25, and the ultrasonic vibration is transmitted along the longitudinal axis C from the proximal direction toward the distal direction in the probe 31. Further, when the ultrasonic vibration is transmitted to the distal treatment section 33, the distal treatment section 33 vibrates in parallel to the longitudinal axis C. In addition, the high frequency current (the high frequency energy) is transmitted to the distal treatment section 33 through the probe side current path, and also transmitted to the jaw conductive member 62 of the jaw 60 through the jaw side current path. When the high frequency current is transmitted to the distal treatment section 33, the distal treatment section 33 functions as the probe electrode portion having the first electric potential E1. In addition, when the high frequency current is transmitted to the jaw conductive member 62, the jaw conductive member 62 functions as the jaw electrode portion having the second electric potential E2 different from the first electric potential E1.

FIG. 15 is a view showing a certain example of a treatment of the grasp object. As shown in FIG. 15, in the treatment in which a blood vessel or the like having a small dimension in the jaw axis direction parallel to the jaw axis J is the grasp object, for example, the grasp object S is brought into contact with the jaw 60 to perform the treatment only in a region where the abutment portion 65, the first non-contact portion 66A and the second non-contact portion 66B are extended in the jaw axis direction. In this case, the entire width insulating portion 81, the proximal side abutment portion 85, the first proximal side non-contact portion 86A and the second proximal side non-contact portion 86B do not come in contact with the grasp object S. Therefore, in a state where the abutment portion 65, the first non-contact portion 66A and the second non-contact portion 66B are in contact with the grasp object S, the grasp object S is grasped between the distal treatment section 33 of the probe 31 and the jaw 60. When the distal treatment section 33 vibrates in this state, frictional heat is generated between the distal treatment section 33 and the grasp object S. By the frictional heat, the grasp object S is cut and simultaneously coagulated. In addition, the high frequency current flows through the grasp object between each of the first non-contact portion 66A and the second non-contact portion 66B and the distal treatment section 33 because the grasp object comes in contact with the distal treatment section 33, the first non-contact portion 66A and the second non-contact portion 66B. In consequence, the grasp object is denatured and coagulation properties of the grasp object improve.

In this case, by the first distance changing portion 72A of the first non-contact portion 66A and the second distance changing portion 72B of the second non-contact portion 66B, the movement of the grasp object along the jaw axis J is regulated. Therefore, in the state where the grasp object S is grasped between the distal treatment section 33 and the jaw 60, the grasp object S does not move along the jaw axis J, and the grasp object S can efficiently be treated.

In addition, the first distance changing portion 72A and the second distance changing portion 72B partially come in contact with the grasp object S. Consequently, a contact area between each of the first non-contact portion 66A and the second non-contact portion 66B (the jaw electrode portion) and the biological tissue decreases. When the contact area between the jaw electrode portion and the grasp object S decreases, a current density of the high frequency current flowing through the grasp object S heightens. In consequence, the coagulation properties of the grasp object S by the high frequency current can improve, and a treatment efficiency of the grasp object by use of the high frequency current can improve.

FIG. 16 is a view showing another example of the treatment of the grasp object. As shown in FIG. 16, in the treatment in which the blood vessel or the like having a small dimension in the jaw axis direction parallel to the jaw axis J is the grasp object, for example, the grasp object S is sometimes brought into contact with the jaw 60 to perform the treatment only in a region where the entire width insulating portion 81 is extended in the jaw axis direction. In this case, the abutment portion 65, the first non-contact portion 66A, the second non-contact portion 66B, the proximal side abutment portion 85, the first proximal side non-contact portion 86A and the second proximal side non-contact portion 86B do not come in contact with the grasp object S. Therefore, in a state where the entire width insulating portion 81 is in contact with the grasp object S, the grasp object S is grasped between the distal treatment section 33 of the probe 31 and the jaw 60. Further, by the frictional heat generated between the distal treatment section 33 and the grasp object S, the grasp object S is cut and simultaneously coagulated. However, the high frequency current does not flow through the grasp object S because the grasp object S is in contact only with the entire width insulating portion 81 that is not the jaw electrode portion.

In this case, the movement of the grasp object S along the jaw axis J is regulated by the first distal side distance changing portion 83A and the second distal side distance changing portion 83B. Therefore, in the state where the grasp object S is grasped between the distal treatment section 33 and the jaw 60, the grasp object S does not move along the jaw axis J, and the grasp object S can efficiently be treated.

As described above, in the state where the grasp object S is in contact only with the abutment portion 65, the first non-contact portion 66A and the second non-contact portion 66B, the treatment is performed by using the ultrasonic vibration and the high frequency current as the energy, and in the state where the grasp object S is in contact only with the entire width insulating portion 81, the treatment is performed by using the only ultrasonic vibration as the energy. That is, even when the high frequency current is transmitted to the jaw conductive member 62, it is possible to select the treatment in which the ultrasonic vibration and the high frequency current are used and the treatment in which the ultrasonic vibration is only used, by changing, along the jaw axis J, a position where the grasp object S comes in contact with the jaw 60.

It is to be noted that, in the treatment in which the ultrasonic vibration and the high frequency current are used, a quantity of heat to be generated by the energy becomes larger and the possibility that the grasp object S is impaired by the heat becomes higher, as compared with the treatment in which the ultrasonic vibration is only used. In consequence, when the high coagulation properties of the grasp object S are not required, the treatment is performed in the state where the grasp object S is brought into contact only with the entire width insulating portion 81.

FIG. 17 is a view showing still another example of the treatment of the grasp object. As shown in FIG. 17, in the treatment in which a membrane tissue or the like having a large dimension in the jaw axis direction parallel to the jaw axis J is the grasp object, for example, the jaw 60 is brought into contact with the grasp object S over a total length of the jaw in the jaw axis direction to perform the treatment. Therefore, in a state where the grasp object S is in contact with the jaw 60 over the total length of the jaw in the jaw axis direction, the grasp object S is grasped between the distal treatment section 33 of the probe 31 and the jaw 60. Further, the grasp object S is cut and simultaneously coagulated by the frictional heat generated between the distal treatment section 33 and the grasp object S. When the high frequency current flows through the grasp object S between the distal treatment section 33 and the jaw conductive member 62, the coagulation properties of the grasp object S are promoted.

In this case, the movement of the grasp object S along the jaw axis J is regulated by the first distance changing portion 72A and the second distance changing portion 72B. Therefore, in the state where the grasp object S is grasped between the distal treatment section 33 and the jaw 60, the grasp object S does not move along the jaw axis J, and the grasp object S can efficiently be treated. In addition, the movement of the grasp object S toward the distal direction is regulated by the first distal side distance changing portion 83A and the second distal side distance changing portion 83B. Consequently, the movement of the grasp object S along the jaw axis J can more effectively be prevented. In addition, the movement of the grasp object S toward the proximal direction is regulated by the first proximal side distance changing portion 87A and the second proximal side distance changing portion 87B. In consequence, the movement of the grasp object S along the jaw axis J can more effectively be prevented.

As described above, in the grasping treatment device 2 of the present embodiment, each of the first continuous surface 67A and the second continuous surface 67B is formed into a shape that does not regulate the movement of the grasp object along the jaw axis J in the state where the grasp object is interposed between the jaw 60 opened relative to the distal treatment section 33 and the distal treatment section 33. Further, the first distance changing portion 72A and the second distance changing portion 72B that are the movement regulating portions are disposed in such positions that they do not come in contact with the grasp object in the state where the grasp object is interposed between the jaw 60 opened relative to the distal treatment section 33 and the distal treatment section 33. Consequently, in the state where the grasp object is interposed between the jaw 60 opened relative to the distal treatment section 33 and the distal treatment section 33, the grasp object can effectively be prevented from being hitched on the jaw 60. Additionally, in the state where the grasp object is grasped between the distal treatment section 33 and the jaw 60, the movement of the grasp object along the jaw axis J can be regulated by the first distance changing portion 72A and the second distance changing portion 72B.

(Modifications)

It is to be noted that, in the first embodiment, the first continuous surface 67A is the curved surface having the curved line shape with the large bending radius R1 in the cross section perpendicular to the first jaw width direction and the second jaw width direction, and the second continuous surface 67B is the curved surface having the curved line shape with the large bending radius R2 in the cross section perpendicular to the first jaw width direction and the second jaw width direction, but the present invention is not limited to this embodiment. For example, in a first modification, as shown in FIG. 18, a first continuous surface 67A may be a flat surface having a linear shape in a cross section perpendicular to a first jaw width direction and a second jaw width direction. Similarly, a second continuous surface 67B may be a flat surface having a straight line shape in the cross section perpendicular to the first jaw width direction and the second jaw width direction. Here, FIG. 18 is a view showing the first continuous surface 67A of the present modification in the cross section perpendicular to the first jaw width direction and the second jaw width direction. Also in the present modification, each of the first continuous surface 67A and the second continuous surface 67B is one continuous surface, and hence in each of the first continuous surface 67A and the second continuous surface 67B, no narrowing sharp portion is formed. Each of the first continuous surface 67A and the second continuous surface 67B is formed into such a shape as described above, and hence in a state where a grasp object is interposed between a jaw 60 opened relative to a distal treatment section 33 and the distal treatment section 33, a movement of the grasp object along a jaw axis J is not regulated by the first continuous surface 67A and the second continuous surface 67B.

According to the first embodiment and the first modification, the first continuous surface 67A is shaped in the form of one surface that forms the first-jaw-width-direction-side edge of the first non-contact portion 66A and is continuous along the jaw axis J. In addition, the second continuous surface 67B is shaped in the form of one surface that forms the second-jaw-width-direction-side edge of the second non-contact portion 66B and is continuous with the jaw axis J. Further, each of the first continuous surface 67A and the second continuous surface 67B is formed into a shape that does not regulate the movement of the grasp object along the jaw axis J in the state where the grasp object is interposed between the jaw 60 opened relative to the distal treatment section 33 and the distal treatment section 33.

Additionally, in the first embodiment, each of the first distance changing portion 72A and the second distance changing portion 72B is provided as the movement regulating portion, but the present invention is not limited to this embodiment. For example, as a second modification, a first distance changing portion 72A may only be provided. In the present modification, a second distance changing portion 72B is not provided in a second wall surface portion 71B of a second non-contact portion 66B. Also in the present modification, similarly to the first embodiment, in a state where a grasp object is grasped between a jaw 60 closed relative to a distal treatment section 33 and the distal treatment section 33, a movement of the grasp object along a jaw axis J is regulated by the first distance changing portion 72A.

According to the first embodiment and the second modification, at least one of the first distance changing portion 72A and the second distance changing portion 72B may be provided. Consequently, in the state where the grasp object is grasped between the jaw 60 closed relative to the distal treatment section 33 and the distal treatment section 33, the movement of the grasp object along the jaw axis J is regulated.

Similarly, at least one of the first distal side distance changing portion 83A and the second distal side distance changing portion 83B may be provided as a distal side distance changing portion. Consequently, in the state where the grasp object is grasped between the jaw 60 closed relative to the distal treatment section 33 and the distal treatment section 33, the movement of the grasp object along the jaw axis J is regulated by the entire width insulating portion 81. In addition, at least one of the first proximal side distance changing portion 87A and the second proximal side distance changing portion 87B may be provided. Consequently, in the state where the grasp object is grasped between the jaw 60 closed relative to the distal treatment section 33 and the distal treatment section 33, the movement of the grasp object along the jaw axis J is regulated by the proximal portion of the jaw 60.

Additionally, in the first embodiment, the end of each of the first concave portions 75A on the first jaw width direction side is formed in a narrowing manner to be sharp in the first distance changing portion 72A, and the end of each of the second concave portions 75B on the second jaw width direction side is formed in a narrowing manner to be sharp in the second distance changing portion 72B, but the present invention is not limited to this embodiment. For example, in a third modification, as shown in FIG. 20, each of first concave portions 75A and second concave portions 75B may be shaped in the form of a curved surface. Also in the present modification, in a state where a grasp object is grasped between a jaw 60 closed relative to a distal treatment section 33 and the distal treatment section 33, movement of the grasp object along a jaw axis J is regulated by a first distance changing portion 72A and a second distance changing portion 72B. In addition, each of the first distance changing portion 72A and the second distance changing portion 72B that are movement regulating portions is formed into such a shape to partially come in contact with the grasp object in the state where the grasp object is grasped between the jaw 60 closed relative to the distal treatment section 33 and the distal treatment section 33. It is to be noted that, also in the present modification, the first distance changing portion 72A and the second distance changing portion 72B are formed in a convex-and-concave manner.

Figure 21:
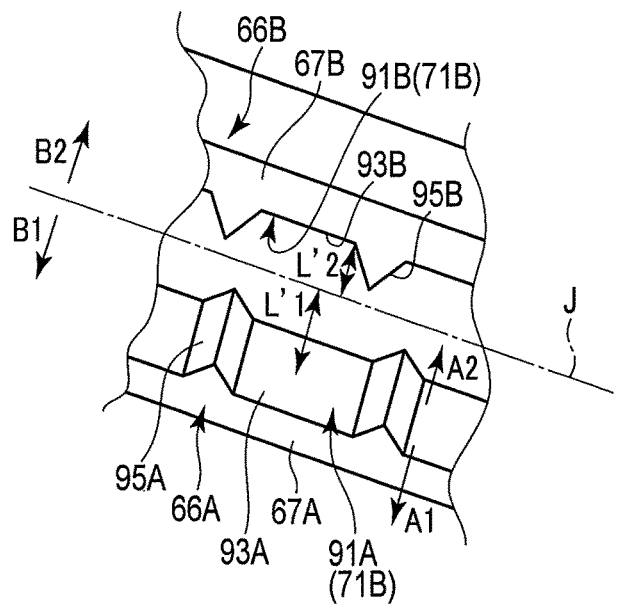
FIG. 21 is a perspective view schematically showing a configuration of a first non-contact portion and a second non-contact portion of a jaw according to a fourth modification.

Additionally, in the first embodiment, there are disposed the first distance changing portion 72A including the first concave portions 75A and the second distance changing portion 72B including the second concave portions 75B, but the present invention is not limited to this embodiment. For example, in a fourth modification, as shown in FIG. 21, a first distance changing portion 91A may be provided in a first wall surface portion 71A facing toward a second jaw width direction (a direction of an arrow B2 of FIG. 21) in a first non-contact portion 66A, and a second distance changing portion 91B may be provided in a second wall surface portion 71B facing toward a first jaw width direction (a direction of an arrow B1 of FIG. 21) in a second non-contact portion 66B. In the first distance changing portion 91A, similarly to a first distance changing portion 72A, a distance from a jaw axis J in the first jaw width direction changes along the jaw axis J. Additionally, in the second distance changing portion 91B, similarly to a second distance changing portion 72B, the distance from the jaw axis J in the second jaw width direction changes along the jaw axis J.

The first distance changing portion 91A includes a first reference surface 93A positioned at a first reference distance L'1 from the jaw axis J in the first jaw width direction. In addition, the first distance changing portion 91A includes first convex portions 95A projecting from the first reference surface 93A toward the second jaw width direction. In each of the first convex portions 95A, the distance from the jaw axis J in the first jaw width direction is smaller than the first reference distance L'1. An end of each of the first convex portions 95A on a second jaw width direction side is formed in a narrowing manner to be sharp. The first distance changing portion 91A is formed in a convex-and-concave manner by the first reference surface 93A and the first convex portions 95A. Due to the abovementioned configuration, in the first distance changing portion 91A that is a movement regulating portion, a movement of a grasp object along the jaw axis J is regulated in a state where the grasp object is grasped between a jaw 60 closed relative to a distal treatment section 33 and the distal treatment section 33. In addition, the first distance changing portion 91A is formed into such a shape to partially come in contact with a grasp object S in the state where the grasp object S is grasped between the jaw 60 closed relative to the distal treatment section 33 and the distal treatment section 33.

The second distance changing portion 91B includes a second reference surface 93B positioned at a second reference distance L'2 from the jaw axis J in the second jaw width direction. In addition, the second distance changing portion 91B includes second convex portions 95B projecting from the second reference surface 93B toward the first jaw width direction. In each of the second convex portions 95B, the distance from the jaw axis J in the second jaw width direction is smaller than the second reference distance L'2. An end of each of the second convex portions 95B on a first jaw width direction side is formed in a narrowing manner to be sharp. The second distance changing portion 91B is formed in a convex-and-concave manner by the second reference surface 93B and the second convex portions 95B. Due to the abovementioned configuration, in the second distance changing portion 91B that is a movement regulating portion, the movement of the grasp object along the jaw axis J is regulated in the state where the grasp object is grasped between the jaw 60 closed relative to the distal treatment section 33 and the distal treatment section 33. In addition, the second distance changing portion 91B is formed into such a shape to partially come in contact with the grasp object S in the state where the grasp object S is grasped between the jaw 60 closed relative to the distal treatment section 33 and the distal treatment section 33.

The first distance changing portion 91A is positioned in the first wall surface portion 71A that is located on the second jaw width direction side with respect to a first continuous surface 67A to face toward the second jaw width direction. Consequently, similarly to the first embodiment, in a state where the grasp object is interposed between the jaw 60 opened relative to the distal treatment section 33 and the distal treatment section 33, the grasp object does not come in contact with the first distance changing portion 91A (the first wall surface portion 71A). In addition, the second distance changing portion 91B is positioned in the second wall surface portion 71B that is located on the first jaw width direction side with respect to a second continuous surface 67B to face toward the first jaw width direction. In consequence, similarly to the first embodiment, the grasp object does not come in contact with the second distance changing portion 91B (the second wall surface portion 71B) in the state where the grasp object is interposed between the jaw 60 opened relative to the distal treatment section 33 and the distal treatment section 33.

It is to be noted that, in the present modification, the first distance changing portion 91A and the second distance changing portion 91B are provided as the movement regulating portions, but at least one of the first distance changing portion 91A and the second distance changing portion 91B may be provided. In consequence, the movement of the grasp object along the jaw axis J is regulated in the state where the grasp object is grasped between the jaw 60 closed relative to the distal treatment section 33 and the distal treatment section 33.

Figure 22:
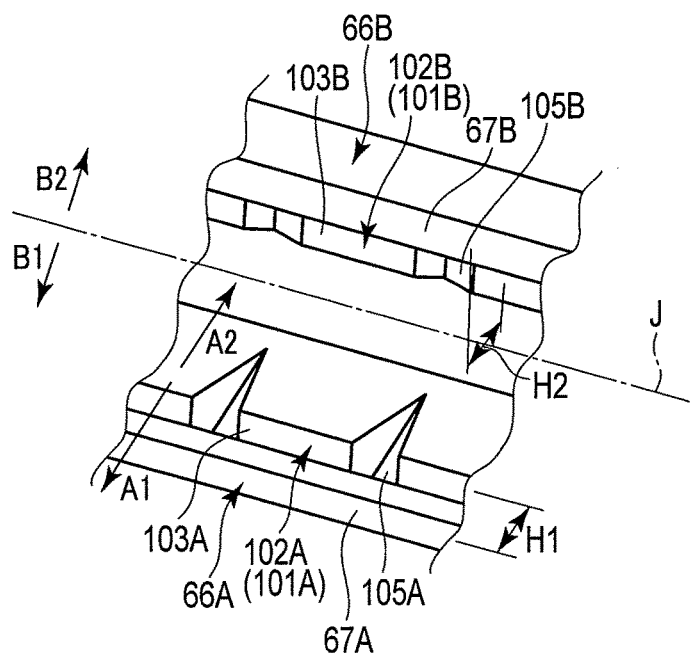
FIG. 22 is a perspective view schematically showing a configuration of a first non-contact portion and a second non-contact portion of a jaw according to a fifth modification.

Additionally, in the first embodiment, the movement regulating portions (the first distance changing portion 72A and the second distance changing portion 72B) are disposed in the first wall surface portion 71A facing in the second jaw width direction and the second wall surface portion 71B facing in the first jaw width direction, but the present invention is not limited to this embodiment. For example, in a fifth modification, as shown in FIG. 22, a first wall surface portion 101A facing toward a jaw closing direction (a direction of an arrow A1 of FIG. 22) may be provided in a first non-contact portion 66A, and a second wall surface portion 101B facing toward the jaw closing direction may be provided in a second non-contact portion 66B. The first wall surface portion 101A is located on a second jaw width direction (a direction of an arrow B2 of FIG. 22) side with respect to a first continuous surface 67A, and the second wall surface portion 101B is located on a first jaw width direction (a direction of an arrow B1 of FIG. 22) side with respect to a second continuous surface 67B.

In the first wall surface portion 101A, a first distance changing portion 102A is provided to be located on a jaw opening direction (a direction of an arrow A2 of FIG. 22) side with respect to the first continuous surface 67A. In the first distance changing portion 102A, a distance from the first continuous surface 67A in the jaw opening direction changes along a jaw axis J. The first distance changing portion 102A includes a first reference surface 103A positioned at a first reference distance H1 from the first continuous surface 67A in the jaw opening direction. In addition, the first distance changing portion 102A includes first concave portions 105A concaved from the first reference surface 103A toward the jaw opening direction. A distance of each of the first concave portions 105A from the first continuous surface 67A in the jaw opening direction is larger than the first reference distance H1. An end of each of the first concave portions 105A on the jaw opening direction side is formed in a narrowing manner to be sharp. The first distance changing portion 102A is formed in a convex-and-concave manner by the first reference surface 103A and the first concave portions 105A.

Due to the abovementioned configuration, in the first distance changing portion 102A, a movement of a grasp object along the jaw axis J is regulated in a state where the grasp object is grasped between a jaw 60 closed relative to a distal treatment section 33 and the distal treatment section 33. That is, the first distance changing portion 102A becomes a movement regulating portion. In addition, the first distance changing portion 102A is formed into such a shape to partially come in contact with the grasp object in the state where the grasp object is grasped between the jaw 60 closed relative to the distal treatment section 33 and the distal treatment section 33.

In addition, the first distance changing portion 102A is positioned in the first wall surface portion 101A that is located on the second jaw width direction side with respect to the first continuous surface 67A to face toward the jaw closing direction, and is located on the jaw opening direction side with respect to the first continuous surface 67A. Consequently, the grasp object does not come in contact with the first distance changing portion 102A in a state where the grasp object is interposed between the jaw 60 opened relative to the distal treatment section 33 and the distal treatment section 33.

In the second wall surface portion 101B, a second distance changing portion 102B is provided to be positioned on the jaw opening direction side with respect to the second continuous surface 67B. In the second distance changing portion 102B, a distance from the second continuous surface 67B in the jaw opening direction changes along the jaw axis J. The second distance changing portion 102B includes a second reference surface 103B positioned at a second reference distance H2 from the second continuous surface 67B in the jaw opening direction. In addition, the second distance changing portion 102B includes second concave portions 105B concaved from the second reference surface 103B toward the jaw opening direction. A distance of each of the second concave portions 105B from the second continuous surface 67B in the jaw opening direction is larger than the second reference distance H2. An end of each of the second concave portions 105B on the jaw opening direction side is formed in a narrowing manner to be sharp. The second distance changing portion 102B is formed in a convex-and-concave manner by the second reference surface 103B and the second concave portions 105B.

Due to the abovementioned configuration, in the second distance changing portion 102B, the movement of the grasp object along the jaw axis J is regulated in the state where the grasp object is grasped between the jaw 60 closed relative to the distal treatment section 33 and the distal treatment section 33. That is, the second distance changing portion 102B becomes a movement regulating portion. In addition, the second distance changing portion 102B is formed into such a shape to partially come in contact with the grasp object in the state where the grasp object is grasped between the jaw 60 closed relative to the distal treatment section 33 and the distal treatment section 33.

In addition, the second distance changing portion 102B is positioned in the second wall surface portion 101B that is located on the first jaw width direction side with respect to the second continuous surface 67B to face in the jaw closing direction, and is positioned on the jaw opening direction side with respect to the second continuous surface 67B. Consequently, the grasp object does not come in contact with the second distance changing portion 102B in the state where the grasp object is interposed between the jaw 60 opened relative to the distal treatment section 33 and the distal treatment section 33.

It is to be noted that, in the present modification, the first distance changing portion 102A and the second distance changing portion 102B are provided as the movement regulating portions, but at least one of the first distance changing portion 102A and the second distance changing portion 102B may be provided. Consequently, the movement of the grasp object along the jaw axis J is regulated in the state where the grasp object is grasped between the jaw 60 closed relative to the distal treatment section 33 and the distal treatment section 33.

Figure 23:
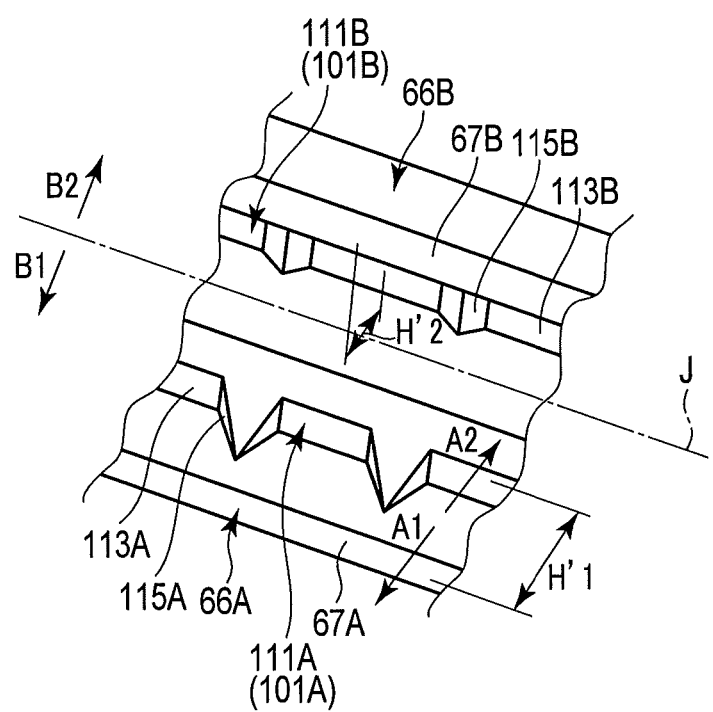
FIG. 23 is a perspective view schematically showing a configuration of a first non-contact portion and a second non-contact portion of a jaw according to a sixth modification.

Additionally, in the fifth modification, the first distance changing portion 102A including the first concave portions 105A and the second distance changing portion 102B including the second concave portions 105B are disposed, but the present invention is not limited to this modification. For example, in a sixth modification, as shown in FIG. 23, a first distance changing portion 111A may be provided in a first wall surface portion 101A facing toward a jaw closing direction (a direction of an arrow A1 of FIG. 23) in a first non-contact portion 66A, and a second distance changing portion 111B may be provided in a second wall surface portion 101B facing toward the jaw closing direction in a second non-contact portion 66B. Similarly to the first distance changing portion 102A, the first distance changing portion 111A is disposed on a jaw opening direction (a direction of an arrow A2 of FIG. 23) side with respect to a first continuous surface 67A, and a distance from the first continuous surface 67A in the jaw opening direction changes along a jaw axis J. In addition, similarly to the second distance changing portion 102B, the second distance changing portion 111B is disposed on the jaw opening direction side with respect to a second continuous surface 67B, and a distance from the second continuous surface 67B in the jaw opening direction changes along the jaw axis J.

The first distance changing portion 111A includes a first reference surface 113A positioned at a first reference distance H'1 from the first continuous surface 67A in the jaw opening direction. In addition, the first distance changing portion 111A includes first convex portions 115A projecting from the first reference surface 113A toward the jaw closing direction. A distance of each of the first convex portions 115A from the first continuous surface 67A in the jaw opening direction is smaller than the first reference distance H'1. An end of each of the first convex portions 115A on the jaw closing direction side is formed in a narrowing manner to be sharp. The first distance changing portion 111A is formed in a convex-and-concave manner by the first reference surface 113A and the first convex portions 115A. Due to the abovementioned configuration, in the first distance changing portion 111A that is a movement regulating portion, a movement of a grasp object along the jaw axis J is regulated in a state where the grasp object is grasped between a jaw 60 closed relative to the distal treatment section 33 and the distal treatment section 33. In addition, the first distance changing portion 111A is formed into such a shape to partially come in contact with a grasp object S in the state where the grasp object S is grasped between the jaw 60 closed relative to the distal treatment section 33 and the distal treatment section 33.

The second distance changing portion 111B includes a second reference surface 113B positioned at a second reference distance H'2 from the second continuous surface 67B in the jaw opening direction. In addition, the second distance changing portion 111B includes second convex portions 115B projecting from the second reference surface 113B toward the jaw closing direction. A distance of each of the second convex portions 115B from the second continuous surface 67B in the jaw opening direction is smaller than the second reference distance H'2. A jaw-closing-direction-side end of each of the second convex portions 115B is formed in a narrowing manner to be sharp. The second distance changing portion 111B is formed in a convex-and-concave manner by the second reference surface 113B and the second convex portions 115B. Due to the abovementioned configuration, in the second distance changing portion 111B that is a movement regulating portion, the movement of the grasp object along the jaw axis J is regulated in the state where the grasp object is grasped between the jaw 60 closed relative to the distal treatment section 33 and the distal treatment section 33. In addition, the second distance changing portion 111B is formed into such a shape to partially come in contact with the grasp object S in the state where the grasp object S is grasped between the jaw 60 closed relative to the distal treatment section 33 and the distal treatment section 33.

The first distance changing portion 111A is positioned in the first wall surface portion 101A that is disposed on a second jaw width direction side with respect to the first continuous surface 67A to face toward the jaw closing direction, and is positioned on the jaw opening direction side with respect to the first continuous surface 67A. In consequence, the grasp object does not come in contact with the first distance changing portion 111A in a state where the grasp object is interposed between the jaw 60 opened relative to the distal treatment section 33 and the distal treatment section 33. In addition, the second distance changing portion 111B is positioned in the second wall surface portion 101B that is located on a first jaw width direction side with respect to the second continuous surface 67B to face in the jaw closing direction, and is positioned on the jaw opening direction side with regard to the second continuous surface 67B. In consequence, the grasp object does not come in contact with the second distance changing portion 111B in the state where the grasp object is interposed between the jaw 60 opened relative to the distal treatment section 33 and the distal treatment section 33.

It is to be noted that, in the present modification, the first distance changing portion 111A and the second distance changing portion 111B are provided as the movement regulating portions, but at least one of the first distance changing portion 111A and the second distance changing portion 111B may be provided. In consequence, the movement of the grasp object along the jaw axis J is regulated in the state where the grasp object is grasped between the jaw 60 closed relative to the distal treatment section 33 and the distal treatment section 33.

According to the abovementioned embodiment and modifications, the movement regulating portion (72A, 72B; 72A; 91A, 91B; 102A, 102B; 111A, 111B) is provided in at least one of a region of the first non-contact portion 66A which is located on the second jaw width direction side with respect to the first continuous surface 67A and a region of the second non-contact portion 66B which is located on the first jaw width direction side with respect to the second continuous surface 67B. In the state where the grasp object is grasped between the jaw 60 closed relative to the distal treatment section 33 and the distal treatment section 33, the movement of the grasp object along the jaw axis J is regulated by the movement regulating portion (72A, 72B; 72A; 91A, 91B; 102A, 102B; 111A, 111B). In addition, the movement regulating portion (72A, 72B; 72A; 91A, 91B; 102A, 102B; 111A, 111B) is positioned at such a position that does not come in contact with the grasp object in the state where the grasp object is interposed between the jaw 60 opened relative to the distal treatment section 33 and the distal treatment section 33. Due to such a constitution, the movement of the grasp object along the jaw axis J can be regulated in the state where the grasp object is grasped between the distal treatment section 33 and the jaw 60. In addition, the grasp object can effectively be prevented from being hitched on the jaw 60 in the state where the grasp object is interposed between the jaw 60 opened relative to the distal treatment section 33 and the distal treatment section 33.

Additionally, in the abovementioned embodiment and modifications, the movement regulating portion (72A, 72B; 72A; 91A, 91B; 102A, 102B; 111A, 111B) is formed into such a shape to partially come in contact with the grasp object in the state where the grasp object is grasped between the jaw 60 closed relative to the distal treatment section 33 and the distal treatment section 33. According to such a constitution, the contact area between each of the first non-contact portion 66A and the second non-contact portion 66B that are the jaw electrode portions and the biological tissue decreases. When the contact area between the jaw electrode portion and the grasp object S decreases, the current density of the high frequency current flowing through the grasp object S heightens. In consequence, the coagulation properties of the grasp object S by the high frequency current can improve, and the treatment efficiency of the grasp object by use of the high frequency current can improve.

Figure 24:
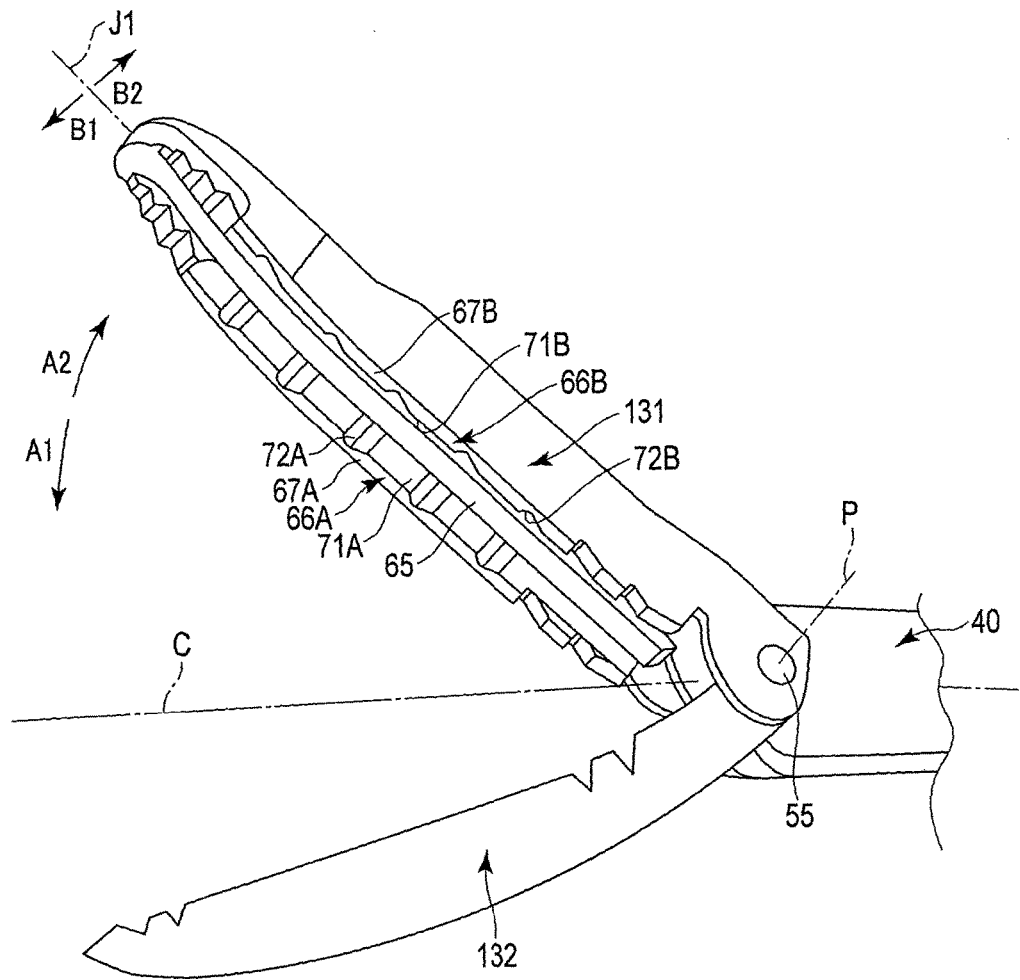
FIG. 24 is a perspective view schematically showing a configuration of a distal portion of a grasping treatment device according to a seventh modification.

Additionally, in a seventh modification shown in FIG. 24, a first grasping member 131 and a second grasping member 132 are attached to a distal portion of a sheath 40 so that the members can turn about a coupling screw 55 (a pivoting axis P). When the first grasping member 131 and the second grasping member 132 pivot, the first grasping member 131 and the second grasping member 132 perform an opening motion or a closing motion relative to each other. When the first grasping member 131 and the second grasping member 132 close relative to each other in a state where a treatment object is interposed between the first grasping member 131 and the second grasping member 132, the treatment object is grasped between the first grasping member 131 and the second grasping member 132. In each of the first grasping member 131 and the second grasping member 132, a conductive portion (not shown) is provided. When a high frequency current is transmitted to the conductive portion of the first grasping member 131 and the conductive portion of the second grasping member 132 in the state where the treatment object is grasped, the high frequency current flows through the treatment object grasped between the first grasping member 131 and the second grasping member 132, and a bipolar treatment is performed. In addition, when the high frequency current is transmitted to the conductive portion of the first grasping member 131 or the conductive portion of the second grasping member 132, a monopolar treatment is also performed. Additionally, in another modification, the high frequency current does not have to be transmitted to the first grasping member 131 and the second grasping member 132.

In the present modification, a configuration similar to the jaw 60 of the first embodiment is applied to the first grasping member 131. That is, in the first grasping member 131, an abutment portion 65 that can abut on the second grasping member 132 is disposed in the same manner as in the jaw 60 of the first embodiment. Further, directions perpendicular to a member axis J1 of the first grasping member 131 and perpendicular to opening and closing directions (a direction of an arrow A1 and a direction of an arrow A2 in FIG. 24) of the first grasping member 131 are a first width direction (a direction of an arrow B1 of FIG. 24) and a second width direction (a direction of an arrow B2 of FIG. 24). In the first grasping member 131, a first non-contact portion 66A is provided on a first width direction side with respect to the abutment portion 65, and a second non-contact portion 66B is provided on a second width direction side with respect to the abutment portion 65. The first non-contact portion 66A and the second non-contact portion 66B are disposed to face the second grasping member 132, and have a space between them and the second grasping member 132 in a state where the abutment portion 65 abuts on the second grasping member 132.

Further, an edge of the first non-contact portion 66A on a first width direction side is formed by the first continuous surface 67A, and an edge of the second non-contact portion 66B is formed by a second continuous surface 67B. Additionally, in the first non-contact portion 66A, a first wall surface portion 71A facing toward the second width direction is disposed, and in the second non-contact portion 66B, a second wall surface portion 71B facing toward the first width direction is disposed. Further, in the first wall surface portion 71A, a first distance changing portion 72A is formed as a movement regulating portion in which a distance from the member axis J1 in the first width direction changes along the member axis J1. Additionally, in the second wall surface portion 71B, a second distance changing portion 72B is formed in which a distance from the member axis J1 in the second width direction changes along the member axis J1.

It is to be noted that, in the present modification, the configuration of the jaw 60 of the first embodiment is applied to the first grasping member 131, but the configuration of the jaw 60 of the first embodiment may be applied to the second grasping member 132. In addition, the configuration of the jaw 60 of the first embodiment may be applied to both of the first grasping member 131 and the second grasping member 132. The configuration of the jaw 60 of one of the first modification to the sixth modification may be applied to the first grasping member 131, and the configuration of the jaw 60 of one of the first modification to the sixth modification may be applied to the second grasping member 132. Furthermore, the configuration of the jaw 60 of one of the first modification to the sixth modification may be applied to both of the first grasping member 131 and the second grasping member 132.

Figure 25:
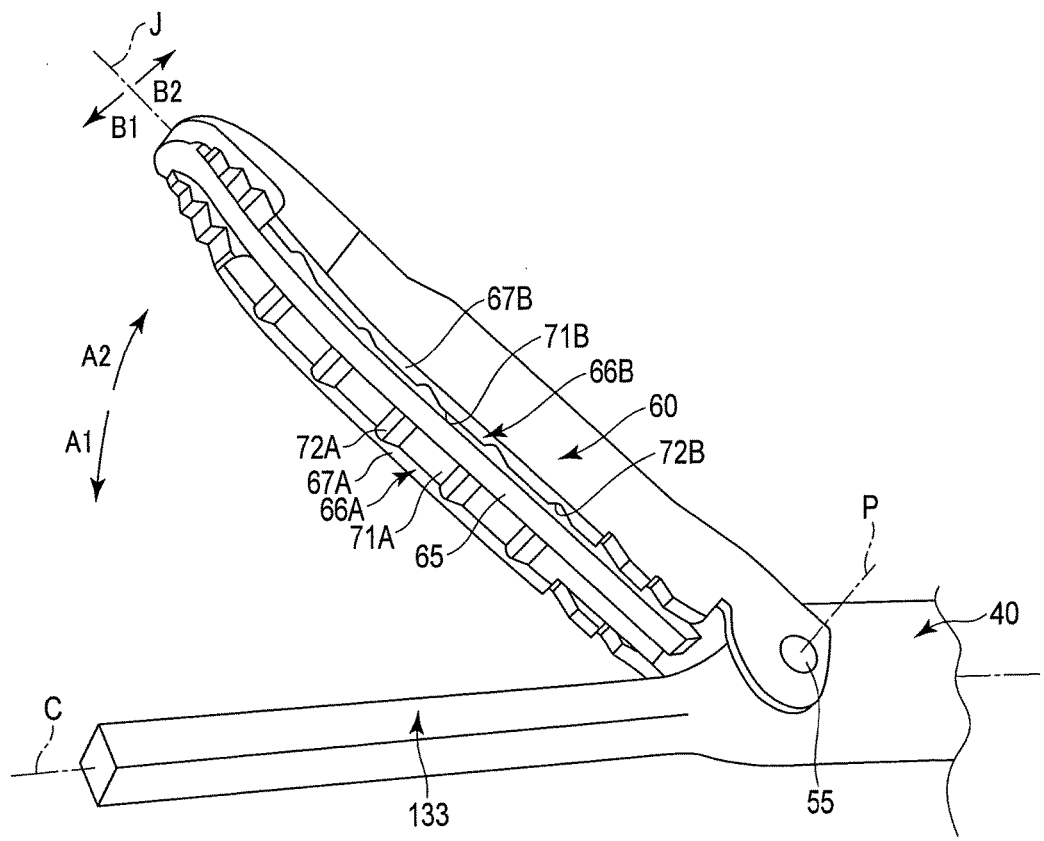
FIG. 25 is a perspective view schematically showing a configuration of a distal portion of a grasping treatment device according to an eighth modification.

Additionally, in an eighth modification shown in FIG. 25, a probe 31 is not provided, and in a sheath 40, a sheath projecting portion 133 is disposed to be extended from a coupling screw 55 (a turning axis P) toward a distal direction. Also in the present modification, similarly to the first embodiment, a jaw 60 is attached to the sheath 40 so that the jaw can turn around the coupling screw 55 (the pivoting axis P). Thus, the jaw 60 pivots, and hence the jaw 60 performs an opening motion or a closing motion relative to the sheath projecting portion 133. When the jaw 60 is closed relative to the sheath projecting portion 133 in a state where a grasp object (a treatment object) is interposed between the jaw 60 and the sheath projecting portion 133, the grasp object is grasped between the jaw 60 and the sheath projecting portion 133. It is to be noted that, in the present modification, energy such as ultrasonic vibration or high frequency current is not transmitted to the sheath projecting portion 133. In addition, the high frequency current is not transmitted to the jaw 60. Additionally, in another modification, the high frequency current may be transmitted to the jaw 60 and the sheath projecting portion 133.

In the present modification, a configuration similar to the jaw 60 of the first embodiment is applied to the jaw 60. That is, in the jaw 60, an abutment portion 65 that can abut on the sheath projecting portion 133 is provided in the same manner as in the jaw 60 of the first embodiment. Further, directions that are perpendicular to a jaw axis J of the jaw 60 and perpendicular to opening and closing directions of the jaw 60 (a direction of an arrow A1 and a direction of an arrow A2 in FIG. 25) are defined as a first width direction (a direction of an arrow B1 of FIG. 25) and a second width direction (a direction of an arrow B2 of FIG. 25). In the jaw 60, a first non-contact portion 66A is provided on a first width direction side with regard to the abutment portion 65, and a second non-contact portion 66B is disposed on a second width direction side with respect to the abutment portion 65. The first non-contact portion 66A and the second non-contact portion 66B are provided to face the sheath projecting portion 133, and have a space between them and the sheath projecting portion 133 in a state where the abutment portion 65 abuts on the sheath projecting portion 133.

Further, a first-width-direction-side edge of the first non-contact portion 66A is formed by a first continuous surface 67A, and a second-width-direction-side edge of the second non-contact portion 66B is formed by a second continuous surface 67B. Additionally, in the first non-contact portion 66A, a first wall surface portion 71A facing in the second width direction is disposed, and in the second non-contact portion 66B, a second wall surface portion 71B facing in the first width direction is disposed. Further, in the first wall surface portion 71A, a first distance changing portion 72A is formed as a movement regulating portion in which a distance from the jaw axis J in the first width direction changes along the jaw axis J. Additionally, in the second wall surface portion 71B, a second distance changing portion 72B is formed in which a distance from the jaw axis J in the second width direction changes along the jaw axis J.

It is to be noted that, in the present modification, the configuration of the jaw 60 of the first embodiment is applied to the jaw 60, but the configuration of the jaw 60 of one of the first modification to the sixth modification may be applied to the jaw 60.

Reference Examples

Hereinafter, reference examples will be described.

Figure 26:
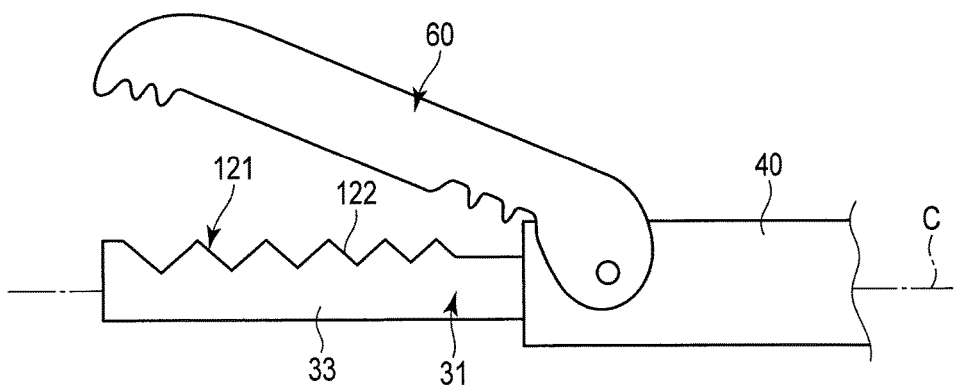
FIG. 26 is a schematic view showing a configuration of a distal portion of a grasping treatment device according to a first reference example.

In a first reference example shown in FIG. 26, similarly to the first embodiment, there are disposed a probe 31 in which an ultrasonic vibration is transmitted up to a distal treatment section 33, and a jaw 60 that is openable and closable relative to the distal treatment section 33. The probe 31 includes a probe side facing portion 121 disposed to face the jaw 60. In the probe side facing portion 121, inclined surfaces 122 inclining relative to a longitudinal axis C are disposed. That is, the inclined surfaces 122 that are not parallel to the longitudinal axis C are disposed. Consequently, when the ultrasonic vibration is transmitted to the distal treatment section 33 in a state where a physiological salt solution is fed to the vicinity of the probe side facing portion 121, cavitation occurs on the inclined surfaces 122.

When a blood vessel in a liver cell or the like is treated, the liver cell is grasped as a grasp object between the distal treatment section 33 and the jaw 60. When the cavitation is caused on the inclined surfaces 122 in this state, the liver cell having low elasticity is shattered and emulsified. When the liver cell is emulsified, the blood vessel in the liver cell is exposed. It is to be noted that the blood vessel having high elasticity is not shattered by the cavitation.

Figure 27:
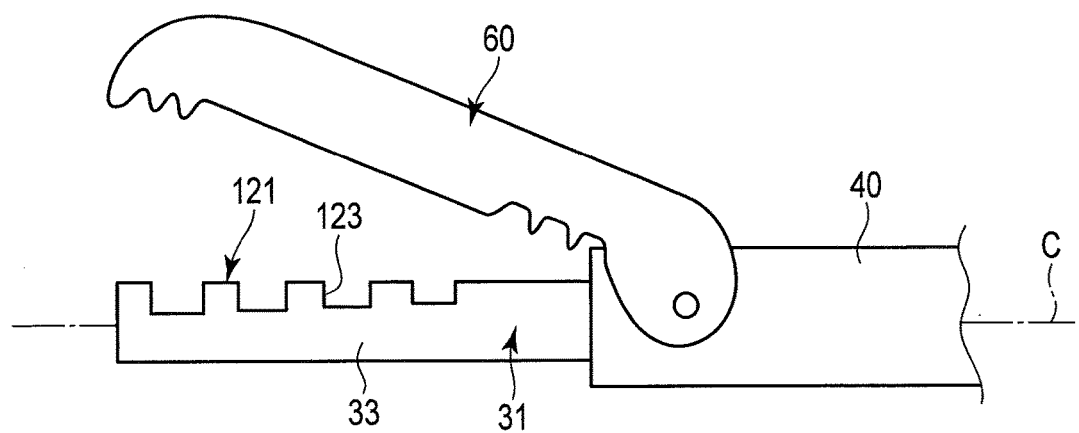
FIG. 27 is a schematic view showing a configuration of a distal portion of a grasping treatment device according to a second reference example.

It is to be noted that, in a second reference example, as shown in FIG. 27, a perpendicular surface 123 perpendicular to a longitudinal axis C may be disposed in a probe side facing portion 121. Also in the present reference example, an ultrasonic vibration is transmitted to a distal treatment section 33 in a state where a physiological salt solution or the like is fed to the vicinity of the probe side facing portion 121, and hence, cavitation occurs on the perpendicular surface 123. That is, in the probe side facing portion 121, there may be disposed at least one of the inclined surface 122 and the perpendicular surface 123 which are not parallel to the longitudinal axis C.

Figure 28:
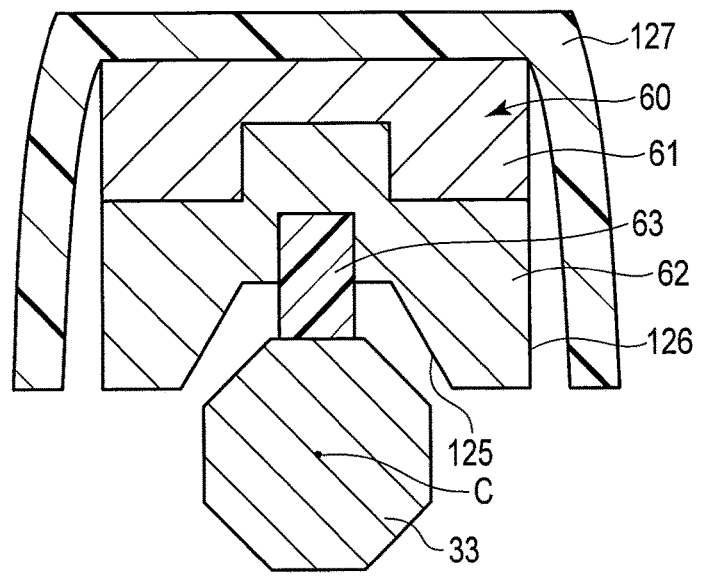
FIG. 28 is a cross-sectional view schematically showing a jaw and a distal treatment section according to a third reference example in a given cross section perpendicular to a longitudinal axis.

Additionally, in a third reference example shown in FIG. 28, similarly to the first embodiment, there are provided a probe 31 in which an ultrasonic vibration is transmitted up to a distal treatment section 33, and a jaw 60 openable and closable relative to the distal treatment section 33. The jaw 60 includes a jaw side facing portion 125 facing the distal treatment section 33. In addition, a region of an outer surface of the jaw 60 except the jaw side facing portion 125 is a non-facing portion 126. The non-facing portion 126 of the jaw 60 is covered with a heat insulating cover 127. The heat insulating cover 127 is made of a material having higher heat insulating properties than materials of a jaw main body 61, a jaw conductive member 62 and a jaw insulating member 63. In addition, the heat insulating cover 127 can be removed from the jaw 60.

In a treatment of a grasp object in which energy such as the ultrasonic vibration or a high frequency current is used, heat is generated by the energy, and a temperature of the jaw 60 heightens. Thus, the non-facing portion 126 of the jaw 60 is covered with the heat insulating cover 127, and hence a biological tissue or the like other than the grasp object does not come in contact with the jaw 60 of the high temperature. Consequently, impairment of the biological tissue or the like other than the grasp object due to the heat is effectively prevented.

Figure 29:
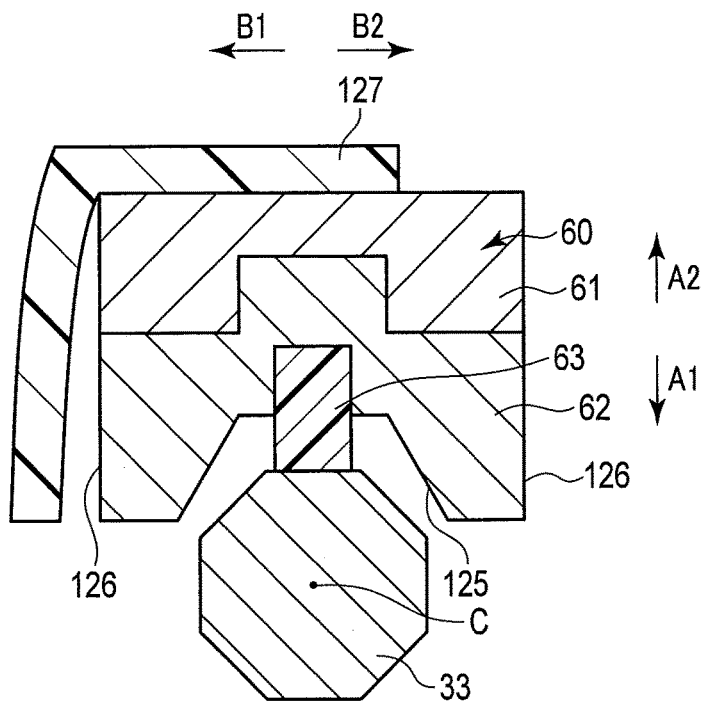
FIG. 29 is a cross-sectional view schematically showing a jaw and a distal treatment section according to a fourth reference example in a given cross section perpendicular to a longitudinal axis.

In a fourth reference example shown in FIG. 29, an only region of a non-facing portion 126 on a first jaw width direction (a direction of an arrow B1 of FIG. 29) side is covered with a heat insulating cover 127. Therefore, a region of the non-facing portion 126 on a second jaw width direction (a direction of an arrow B2 of FIG. 29) side is not covered with the heat insulating cover 127. Here, the second jaw width direction coincides with a direction in which a jaw 60 and a distal treatment section 33 are moved in a treatment. Consequently, a biological tissue or the like on the second jaw width direction side with respect to the jaw 60 will be grasped as a grasp object by moving the jaw 60 from a current position.

Figure 30:
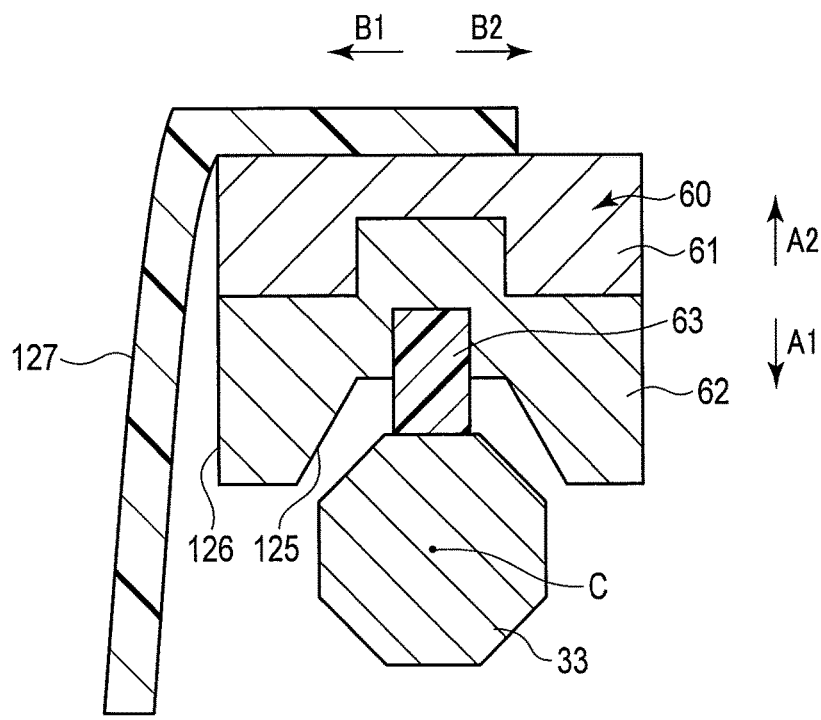
FIG. 30 is a cross-sectional view schematically showing a jaw and a distal treatment section according to a fifth reference example in a given cross section perpendicular to a longitudinal axis.

In a fifth reference example shown in FIG. 30, a heat insulating cover 127 is extended up to a region located on a jaw closing direction (a direction of an arrow A1 of FIG. 30) side with respect to the distal treatment section 33 of a probe 31. Consequently, a region of an outer surface of the distal treatment section 33 on a first jaw width direction side is covered with the heat insulating cover 127. In a treatment of a grasp object in which energy such as an ultrasonic vibration and a high frequency current are used, heat generated by the energy raises a temperature of the distal treatment section 33 in addition to the jaw 60. Thus, the outer surface of the distal treatment section 33 is covered with the heat insulating cover 127, and hence, a biological tissue or the like other than the grasp object does not come in contact with the distal treatment section 33 having the high temperature. In consequence, impairment of the biological tissue or the like other than the grasp object due to the heat is further effectively prevented.

Hereinafter, characteristic matters will be added.

Notes (Additional Note 1)

A grasping unit which is extended along a jaw axis, which is openable and closable relative to a distal treatment section provided in a probe in jaw opening and closing directions perpendicular to the jaw axis, and which is capable of grasping a grasp object between the grasping unit and the distal treatment section in a state where the grasping unit is closed relative to the distal treatment section, the grasping unit comprising:

an abutment portion configured to abut on the distal treatment section in the state where the grasping unit is closed relative to the distal treatment section;

a first non-contact portion which is provided on a first jaw width direction side with respect to the abutment portion to face the distal treatment section, and which has a space between the first non-contact portion and the distal treatment section in a state where the abutment portion abuts on the distal treatment section, directions that are perpendicular to the jaw axis and perpendicular to the jaw opening and closing directions being defined as a first jaw width direction and a second jaw width direction;

a second non-contact portion which is provided on the second jaw width direction side with respect to the abutment portion to face the distal treatment section, and which has the space between the second non-contact portion and the distal treatment section in the state where the abutment portion abuts on the distal treatment section;

a first continuous surface which forms an edge of the first non-contact portion on the first jaw width direction side, and which is shaped in a form of one surface continuous along the jaw axis, the first continuous surface being formed into a shape that does not regulate a movement of the grasp object along the jaw axis in a state where the grasp object is interposed between the grasping unit opened relative to the distal treatment section and the distal treatment section;

a second continuous surface which forms an edge of the second non-contact portion on a second jaw width direction side, and which is shaped in a form of one surface continuous along the jaw axis, the second continuous surface being formed into a shape that does not regulate the movement of the grasp object along the jaw axis in the state where the grasp object is interposed between the grasping unit opened relative to the distal treatment section and the distal treatment section; and a movement regulating portion which is provided in at least one of a region of the first non-contact portion located on the second jaw width direction side with respect to the first continuous surface and a region of the second non-contact portion located on the first jaw width direction side with respect to the second continuous surface, and which is configured to regulate the movement of the grasp object along the jaw axis in a state where the grasp object is grasped between the grasping unit closed relative to the distal treatment section and the distal treatment section, the movement regulating portion being positioned at a position that does not come in contact with the grasp object in the state where the grasp object is interposed between the grasping unit opened relative to the distal treatment section and the distal treatment section.

(Additional Note 2)

A grasping treatment device comprising:

the grasping unit of additional note 1; and the probe extended along a longitudinal axis and including the distal treatment section in a distal portion thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment device comprising:
a probe which includes a distal treatment section in a distal portion thereof;
a jaw which extends from a proximal side toward a distal side along a longitudinal axis of the jaw, and which is openable and closable relative to the distal treatment section in jaw opening and closing directions that are transverse to a direction along the longitudinal axis of the jaw;
an abutment portion which is disposed in the jaw, and which is configured to abut on the distal treatment section by closing the jaw relative to the distal treatment section; and
a first non-contact portion that faces the distal treatment section and is provided on a first side of the abutment portion in a jaw width direction that is transverse to the jaw opening and closing directions and to the longitudinal axis, the first non-contact portion being spaced from the distal treatment section in a state where the abutment portion abuts on the distal treatment section,
wherein the first non-contact portion comprises:
a first continuous surface which forms an outer edge of the first non-contact portion in the jaw width direction, and which has a continuously curved shape along a length of the first non-contact portion when viewed in cross section perpendicular to both the jaw width direction and the longitudinal axis;
a first wall surface provided between the first continuous surface and the abutment portion in the jaw width direction, and which faces the abutment portion;
a first movement regulating portion formed in the first wall surface and having a convex and concave shape in the direction along the longitudinal axis, the first movement regulating portion being configured to regulate a movement of a tissue grasped between the jaw and the distal treatment section in the direction along the longitudinal axis.

2. The grasping treatment device of claim 1, wherein:
the distal treatment section is made of a conductive material, and is configured to function as a probe electrode portion having a first electric potential when a high frequency current is transmitted thereto,
the abutment portion is made of an electrically insulating material, the first non-contact portion is made of a conductive material, and is configured to function as a jaw electrode portion having a second electric potential different from the first electric potential when the high frequency current is transmitted thereto, and the first movement regulating portion is configured to partially come in contact with the tissue when the tissue is grasped between the jaw and the distal treatment section.

3. The grasping treatment device of claim 2, wherein:

the probe is configured to transmit an ultrasonic vibration to the distal treatment section from a proximal direction toward a distal direction, the jaw includes an entire width insulating portion which faces the distal treatment portion and is provided distal to the first non-contact portion, and which is made of an electrically insulating material over an entire width of the jaw in the jaw width direction, and the entire width insulating portion includes a distal portion of the abutment portion.

4. The grasping treatment device of claim 3, wherein the entire width insulating portion has higher slipping properties with respect to the tissue than the first non-contact portion.

5. The grasping treatment device of claim 1, wherein the first movement regulating portion includes a distance changing portion in which a distance from the longitudinal axis of the jaw to the first wall surface changes in accordance with positions in the direction along the longitudinal axis of the jaw.

6. The grasping treatment device of claim 1, wherein:

the jaw further includes a second non-contact portion that faces the distal treatment section and is provided on a second side of the abutment portion in the jaw width direction opposite to the first side, the second non-contact portion being spaced from the distal treatment section in the state where the abutment portion abuts on the distal treatment section, wherein the second non-contact portion comprises:

a second continuous surface which forms an outer edge of the second non-contact portion in the jaw width direction, and which has a continuously curved shape along a length of the second non-contact portion when viewed in cross section perpendicular to both the jaw width direction and the longitudinal axis;

a second wall surface provided between the second continuous surface and the abutment portion in the jaw width direction, and which faces the abutment portion; and a second movement regulating portion formed in the second wall surface and having a convex and concave shape in the direction along the longitudinal axis, the second movement regulating portion being configured to regulate the movement of the tissue grasped between the jaw and the distal treatment section in the direction along the longitudinal axis.

* * * * *